United States Patent
Astakhova

(10) Patent No.: US 12,257,294 B2
(45) Date of Patent: Mar. 25, 2025

(54) THERAPEUTICS FOR AUTOIMMUNE DISEASE: SYNTHETIC ANTIGENS

(71) Applicant: DANMARKS TEKNISKE UNIVERSITET, Kgs. Lyngby (DK)

(72) Inventor: Kira Astakhova, Copenhagen SV (DK)

(73) Assignee: DANMARKS TEKNISKE UNIVERSITET, Kongens Lyngby (DK)

( * ) Notice: Subject to any disclaimer, the term of this patent is extended or adjusted under 35 U.S.C. 154(b) by 830 days.

(21) Appl. No.: 16/966,184

(22) PCT Filed: Feb. 4, 2019

(86) PCT No.: PCT/EP2019/052677
§ 371 (c)(1),
(2) Date: Jul. 30, 2020

(87) PCT Pub. No.: WO2019/149946
PCT Pub. Date: Aug. 8, 2019

(65) Prior Publication Data
US 2022/0193210 A1 Jun. 23, 2022

(30) Foreign Application Priority Data
Feb. 2, 2018 (EP) .................... 18154924

(51) Int. Cl.
| | | |
|---|---|---|
| A61K 39/00 | (2006.01) | |
| A61K 9/51 | (2006.01) | |
| A61K 31/728 | (2006.01) | |
| A61K 47/36 | (2006.01) | |
| A61K 47/60 | (2017.01) | |
| A61P 37/06 | (2006.01) | |
| A61K 47/69 | (2017.01) | |

(52) U.S. Cl.
CPC ........ *A61K 39/0008* (2013.01); *A61K 9/5161* (2013.01); *A61K 31/728* (2013.01); *A61K 47/36* (2013.01); *A61K 47/60* (2017.08); *A61P 37/06* (2018.01); *A61K 2039/6018* (2013.01); *A61K 2039/6087* (2013.01); *A61K 2039/627* (2013.01); *A61K 47/6939* (2017.08)

(58) Field of Classification Search
CPC .............. A61K 39/0008; A61K 9/5161; A61K 31/728; A61K 47/36; A61K 47/60; A61K 47/6939; A61K 2039/6018; A61K 2039/6087; A61P 37/06
See application file for complete search history.

(56) References Cited

U.S. PATENT DOCUMENTS 5,700,641 A * 12/1997 Salonen ............ C12Q 1/6883
435/6.12
2015/0359865 A1 12/2015 Kishimoto
2017/0182177 A1 6/2017 Rana
2017/0348415 A1* 12/2017 Hoge .................. A61K 39/36

FOREIGN PATENT DOCUMENTS

WO WO 2007/011967 1/2007

OTHER PUBLICATIONS

Alibolandi et al., Smart AS1411-aptamer conjugated pegylated PAMAM dendrimer for the superior delivery of camptothecin to colon adenocarcinoma in vitro and in vivo. Int J Pharm. Mar. 15, 2017;519(1-2):352-364.
Ayatollahi et al., Aptamer-targeted delivery of Bcl-XL shRNA using alkyl modified PAMAM dendrimers into lung cancer cells. Int J Biochem Cell Biol. Nov. 2017;92:210-217.
Cravedi. Role of monoclonal antibodies in the treatment of immune-mediated kidney disease: the state of the art. G Ital Nefrol. May-Jun. 2012;29(3):274-82; discussion 292. Translated abstract only. 1 page.
Ehrenstein et al., Human IgG anti-DNA antibodies deposit in kidneys and induce proteinuria in SCID mice. Kidney Int. Sep. 1995;48(3):705-11.
Elkon et al., Nature and functions of autoantibodies. Nat Clin Pract Rheumatol. Sep. 2008;4(9):491-8.
Giannella et al., Circulating levels and characterization of microparticles in patients with different degrees of glucose tolerance. Cardiovasc Diabetol. Sep. 19, 2017;16(1):118.
Huang et al., Both systemic and local lipopolysaccharide (LPS) burden are associated with knee OA severity and inflammation. Osteoarthritis Cartilage. Oct. 2016;24(10):1769-1775.
Hutchinson et al., Peptide hormones and lipopeptides: from self-assembly to therapeutic applications. J Pept Sci. Feb. 2017;23(2):82-94.
International Search Report and Written Opinion for PCT/EP2019/052677. Mailed May 17, 2019. 11 pages.
Juliano et al., Integrin targeted delivery of gene therapeutics. Theranostics. Mar. 2, 2011;1:211-9.
Kesharwani et al., Dendrimer as nanocarrier for drug delivery. Progress in Polymer Science, 2014 vol. 39, No. 2, pp. 268-307.

(Continued)

*Primary Examiner* — Louise W Humphrey
*Assistant Examiner* — Anjali Ajit Hirani
(74) *Attorney, Agent, or Firm* — Lisa Mueller; Casimir Jones SC

(57) ABSTRACT

The present invention concerns therapeutics for autoimmune diseases and provides removal of inflammation-causing autoantibodies. In order to target the disease in the most efficient manner, a nanoconjugate complex is provided, comprising at least one specific antigen component recognized by autoantibodies related to the autoimmune disease, at least one helper moiety, and a nanoparticle carrier connecting the components. Each component of the therapeutic nanoconjugate complex has a specific function, yielding a nanoconjugate complex which facilitates specific binding, forming a stable antibody-therapeutic complex in the blood stream and rapid clearance of this complex to the liver.

6 Claims, 15 Drawing Sheets

Specification includes a Sequence Listing.

(56) References Cited

OTHER PUBLICATIONS

Luong et al., PEGylated PAMAM dendrimers: Enhancing efficacy and mitigating toxicity for effective anticancer drug and gene delivery. Acta Biomater. Oct. 1, 2016;43:14-29.
Mason et al., A human anti-dsDNA monoclonal antibody caused hyaline thrombi formation in kidneys of 'leaky' SCID mice. Clin Exp Immunol. Oct. 2001;126(1):137-42.
Muller. Histone Autoantibodies. Autoantibodies (third edition), Elsevier. 2014; chapter23, p. 195-201.
Patton. Development and Applications of Click Chemistry. Nov. 8, 2004. 8 pages.
Yang et al., Models of chronic kidney disease. Drug Discov Today Dis Models. 2010;7(1-2):13-19.

\* cited by examiner

1

R = G5 PAMAM

2

R = G5 PAMAM

3

R = G5 PAMAM

4

R = G5 PAMAM

5

R = G5 PAMAM

6

R = G5 PAMAM

7

R = G5 PAMAM

8

R = G5 PAMAM

9

R = G5 PAMAM

10

R = G5 PAMAM

NANOSIGHT

CH 2018-12-20 15-31-17

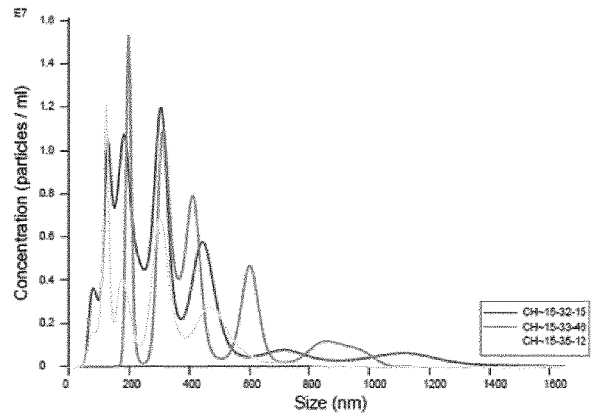
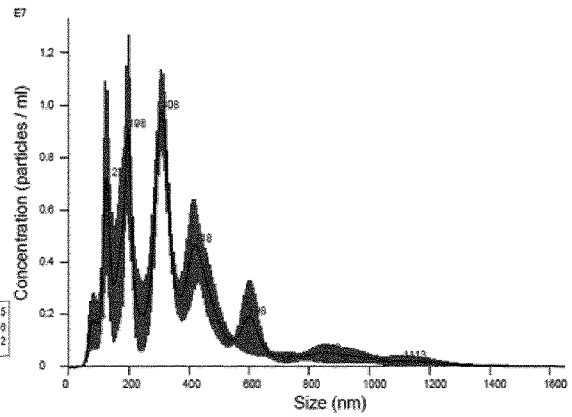

FTLA Concentration / Size graph for Experiment:
CH 2018-12-20 15-31-17

Averaged FTLA Concentration / Size for Experiment:
CH 2018-12-20 15-31-17
Error bars indicate +/-1 standard error of the mean

Results

Stats: Merged Data
Mean:           364.2 nm
Mode:           308.2 nm
SD:             225.4 nm
D10:            128.2 nm
D50:            310.1 nm
D90:            623.2 nm Stats: Mean +/- Standard Error
Mean:           360.4 +/- 40.3 nm
Mode:           208.5 +/- 52.9 nm
SD:             204.1 +/- 29.6 nm
D10:            144.0 +/- 26.1 nm
D50:            318.0 +/- 30.2 nm
D90:            653.7 +/- 84.1 nm
Concentration:  4.43e+008 +/- 8.63e+007 particles/ml
                22.5 +/- 4.4 particles/frame
                31.1 +/- 4.9 centres/frame

FIGURE 10A

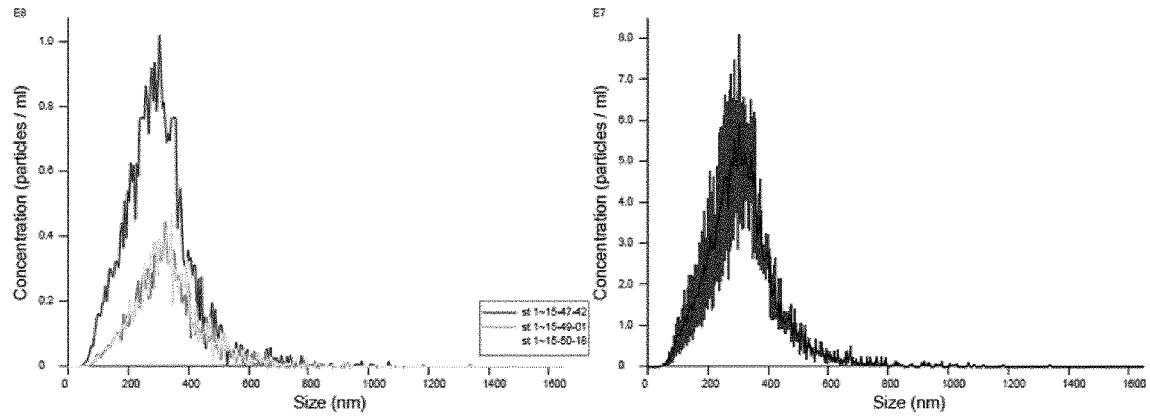

NANOSIGHT st 1 2018-12-20 15-47-19

Concentration / Size graph for Experiment:
st 1 2018-12-20 15-47-19

Averaged Concentration / Size for Experiment:
st 1 2018-12-20 15-47-19
Error bars indicate +/-1 standard error of the mean

Results

Stats: Merged Data
Mean:           312.7 nm
Mode:           303.4 nm
SD:             116.3 nm
D10:            173.1 nm
D50:            298.4 nm
D90:            446.0 nm Stats: Mean +/- Standard Error
Mean:           319.1 +/- 10.0 nm
Mode:           322.7 +/- 11.2 nm
SD:             115.4 +/- 3.6 nm
D10:            180.4 +/- 9.1 nm
D50:            305.0 +/- 9.7 nm
D90:            451.0 +/- 13.6 nm
Concentration:  2.39e+009 +/- 7.94e+008 particles/ml
                121.1 +/- 40.3 particles/frame
                132.0 +/- 42.3 centres/frame

FIGURE 10B

SEQUENCE LISTING

<160> NUMBER OF SEQ ID NOS: 33

<210> SEQ ID NO 1
<211> LENGTH: 17
<212> TYPE: DNA

```
<213> ORGANISM: Artificial sequence
<220> FEATURE:
<223> OTHER INFORMATION: Synthesized sequence
<220> FEATURE:
<221> NAME/KEY: misc_feature
<222> LOCATION: (1)..(17)
<223> OTHER INFORMATION: Specific DNA-antigen targeted by anti-DNA
      antibodies in SLE disease

<400> SEQUENCE: 1
tcctttcttt ctttctt                                                       17

<210> SEQ ID NO 2
<211> LENGTH: 28
<212> TYPE: DNA
<213> ORGANISM: Artificial sequence
<220> FEATURE:
<223> OTHER INFORMATION: Synthesized sequence
<220> FEATURE:
<221> NAME/KEY: misc_feature
<223> OTHER INFORMATION: Specific DNA-antigen targeted by anti-DNA
      antibodies in SLE disease
<220> FEATURE:
<221> NAME/KEY: misc_feature
<222> LOCATION: (1)..(28)
<223> OTHER INFORMATION: Specific DNA-antigen targeted by anti-DNA
      antibodies in SLE disease

<400> SEQUENCE: 2
ttagggttag ggttagggtt agggttag                                           28

<210> SEQ ID NO 3
<211> LENGTH: 19
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(19)
<223> OTHER INFORMATION: Specific peptide antigen mimicking histone H3
      peptides to bind to antinuclear antibodies

<400> SEQUENCE: 3

Ala Arg Thr Lys Gln Thr Ala Arg Lys Ser Thr Gly Gly Lys Ala Pro
1               5                   10                  15

Gly Gly Cys

<210> SEQ ID NO 4
<211> LENGTH: 18
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(18)
<223> OTHER INFORMATION: P41, liver targeting peptide

<400> SEQUENCE: 4

Ser Trp Leu Arg Arg Ile Trp Arg Trp Ile Cys Lys Val Leu Ser Arg
1               5                   10                  15

Phe Lys

<210> SEQ ID NO 5
<211> LENGTH: 8
<212> TYPE: PRT
<213> ORGANISM: Artificial sequence
<220> FEATURE:
```

```
<223> OTHER INFORMATION: Synthesized sequence
<220> FEATURE:
<221> NAME/KEY: MISC_FEATURE
<222> LOCATION: (1)..(8)
<223> OTHER INFORMATION: Specific peptide antigen mimicking histone H3
      peptides (partial) to bind to antinuclear antibodies. The peptide
      is acetylated at the N-terminal.

<400> SEQUENCE: 5

Ala Arg Thr Lys Gln Thr Ala Arg
1               5

<210> SEQ ID NO 6
<211> LENGTH: 14
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(14)
<223> OTHER INFORMATION: Specific peptide antigen mimicking histone H3
      peptides (partial) to bind to antinuclear antibodies. The peptide
      is acetylated at the N-terminal.

<400> SEQUENCE: 6

Lys Gln Thr Ala Arg Lys Ser Thr Gly Gly Lys Ala Pro Gly
1               5                   10

<210> SEQ ID NO 7
<211> LENGTH: 24
<212> TYPE: DNA
<213> ORGANISM: Artificial sequence
<220> FEATURE:
<223> OTHER INFORMATION: Synthesized sequence
<220> FEATURE:
<221> NAME/KEY: misc_feature
<222> LOCATION: (1)..(14)
<223> OTHER INFORMATION: Antigen

<400> SEQUENCE: 7
atcgatcgat cgatcgatcg atcg                                            24

<210> SEQ ID NO 8
<211> LENGTH: 24
<212> TYPE: DNA
<213> ORGANISM: Artificial sequence
<220> FEATURE:
<223> OTHER INFORMATION: Synthesized sequence
<220> FEATURE:
<221> NAME/KEY: misc_feature
<222> LOCATION: (1)..(24)
<223> OTHER INFORMATION: antigen

<400> SEQUENCE: 8
tccttccttc cttccttcct tcct                                            24

<210> SEQ ID NO 9
<211> LENGTH: 21
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(21)
<223> OTHER INFORMATION: Potential peptide epitope; Xaa is citrulline
      (IUPAC name: 2-amino-5-(carbamoylamino)pentanoic acid)

<400> SEQUENCE: 9
```

His His Pro Gly Ile Ala Glu Phe Pro Ser Xaa Gly Lys Ser Ser Ser
1               5                   10                  15

Tyr Ser Lys Gln Phe
            20

<210> SEQ ID NO 10
<211> LENGTH: 21
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(21)
<223> OTHER INFORMATION: potential peptide epitope; Xaa is citrulline
      (IUPAC name: 2-amino-5-(carbamoylamino)pentanoic acid)

<400> SEQUENCE: 10

His His Pro Gly Ile Ala Glu Phe Pro Ser Xaa Gly Lys Ser Tyr Ser
1               5                   10                  15

Tyr Ser Lys Gln Phe
            20

<210> SEQ ID NO 11
<211> LENGTH: 21
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(21)
<223> OTHER INFORMATION: potential peptide epitope; Xaa is citrulline
      (IUPAC name: 2-amino-5-(carbamoylamino)pentanoic acid)

<400> SEQUENCE: 11

His Gly Pro Gly Ile Ala Glu Phe Pro Ser Xaa Gly Pro Ser Tyr Ser
1               5                   10                  15

Tyr Ser Lys Gln Phe
            20

<210> SEQ ID NO 12
<211> LENGTH: 21
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(21)
<223> OTHER INFORMATION: potential peptide epitope; Xaa is citrulline
      (IUPAC name: 2-amino-5-(carbamoylamino)pentanoic acid)

<400> SEQUENCE: 12

His Gly Ile Gly Leu Ala Glu Phe Pro Ser Xaa Gly Lys Ile Ser Ala
1               5                   10                  15

Tyr Ser Lys Gln Phe
            20

<210> SEQ ID NO 13
<211> LENGTH: 21
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(21)

```
<223> OTHER INFORMATION: potential peptide epitope; Xaa is citrulline
      (IUPAC name: 2-amino-5-(carbamoylamino)pentanoic acid)

<400> SEQUENCE: 13

His Gly Pro Gly Gly Ala Glu Phe Pro Ser Xaa Gly Lys Ala Tyr Ser
1               5                   10                  15

Tyr Gly Lys Gln Phe
            20

<210> SEQ ID NO 14
<211> LENGTH: 13
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(13)
<223> OTHER INFORMATION: potential peptide epitope; Xaa is citrulline
      (IUPAC name: 2-amino-5-(carbamoylamino)pentanoic acid)

<400> SEQUENCE: 14

Ala Glu Gly Gly Gly Val Xaa Gly Pro Arg Val Val Glu
1               5                   10

<210> SEQ ID NO 15
<211> LENGTH: 13
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(13)
<223> OTHER INFORMATION: potential peptide epitope; Xaa is citrulline
      (IUPAC name: 2-amino-5-(carbamoylamino)pentanoic acid)

<400> SEQUENCE: 15

Ala Ser Ser Gly Gly Val Xaa Gly Pro Arg Ile Val Glu
1               5                   10

<210> SEQ ID NO 16
<211> LENGTH: 13
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(13)
<223> OTHER INFORMATION: potential peptide epitope; Xaa is citrulline
      (IUPAC name: 2-amino-5-(carbamoylamino)pentanoic acid)

<400> SEQUENCE: 16

Ala Glu Gly Ala Ser Val Xaa Gly Pro Arg Val Val Glu
1               5                   10

<210> SEQ ID NO 17
<211> LENGTH: 16
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(16)
<223> OTHER INFORMATION: potential peptide epitope; Xaa is citrulline
      (IUPAC name: 2-amino-5-(carbamoylamino)pentanoic acid)

<400> SEQUENCE: 17
```

-continued

```
Lys Asp Leu Leu Pro Ser Xaa Asp Xaa Gln His Leu Pro Leu Ile Lys
1               5                   10                  15

<210> SEQ ID NO 18
<211> LENGTH: 16
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(16)
<223> OTHER INFORMATION: potential peptide epitope; Xaa is citrulline
      (IUPAC name: 2-amino-5-(carbamoylamino)pentanoic acid)

<400> SEQUENCE: 18

Lys Asp Leu Leu Pro Ser Xaa Asp Gly Gln His Leu Pro Leu Ile Lys
1               5                   10                  15

<210> SEQ ID NO 19
<211> LENGTH: 16
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(16)
<223> OTHER INFORMATION: potential peptide epitope; Xaa is citrulline
      (IUPAC name: 2-amino-5-(carbamoylamino)pentanoic acid)

<400> SEQUENCE: 19

Lys Asp Leu Leu Pro Ser Xaa Asp Xaa Gly Ala Ile Pro Leu Ile Lys
1               5                   10                  15

<210> SEQ ID NO 20
<211> LENGTH: 23
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(23)
<223> OTHER INFORMATION: potential peptide epitope; Xaa is citrulline
      (IUPAC name: 2-amino-5-(carbamoylamino)pentanoic acid)

<400> SEQUENCE: 20

Gln Met Arg Met Glu Leu Glu Xaa Pro Gly Gly Asn Glu Ile Thr Xaa
1               5                   10                  15

Gly Gly Ser Thr Ser Tyr Gly
            20

<210> SEQ ID NO 21
<211> LENGTH: 14
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(14)
<223> OTHER INFORMATION: potential peptide epitope; Xaa is citrulline
      (IUPAC name: 2-amino-5-(carbamoylamino)pentanoic acid)

<400> SEQUENCE: 21

Asn Val Ser Pro Gly Thr Xaa Xaa Glu Tyr His Thr Glu Lys
1               5                   10
```

```
<210> SEQ ID NO 22
<211> LENGTH: 14
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(14)
<223> OTHER INFORMATION: potential peptide epitope; Xaa is citrulline
      (IUPAC name: 2-amino-5-(carbamoylamino)pentanoic acid)

<400> SEQUENCE: 22

Asn Val Ala Tyr Pro Thr Xaa Xaa Glu Tyr His Gly Glu Lys
1               5                   10

<210> SEQ ID NO 23
<211> LENGTH: 16
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(16)
<223> OTHER INFORMATION: potential peptide epitope; Xaa is citrulline
      (IUPAC name: 2-amino-5-(carbamoylamino)pentanoic acid)

<400> SEQUENCE: 23

Ser Thr Xaa Ser Val Ser Ser Ser Ser Tyr Xaa Xaa Met Phe Gly Gly
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(15)
<223> OTHER INFORMATION: potential peptide epitope; Xaa is citrulline
      (IUPAC name: 2-amino-5-(carbamoylamino)pentanoic acid)

<400> SEQUENCE: 24

Ala Ala Pro Val Ser Gly Ser Ser Tyr Xaa Xaa Met Phe Gly Gly
1               5                   10                  15

<210> SEQ ID NO 25
<211> LENGTH: 16
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(16)
<223> OTHER INFORMATION: potential peptide epitope; Xaa is citrulline
      (IUPAC name: 2-amino-5-(carbamoylamino)pentanoic acid)

<400> SEQUENCE: 25

Ser Thr Xaa Ser Val Ser Ser Ser Ser Tyr Lys Gly Ala Phe Leu Gly
1               5                   10                  15

<210> SEQ ID NO 26
<211> LENGTH: 16
<212> TYPE: PRT
<213> ORGANISM: Artificial sequence
<220> FEATURE:
<223> OTHER INFORMATION: Synthesized sequence
```

```
<220> FEATURE:
<221> NAME/KEY: MISC_FEATURE
<222> LOCATION: (1)..(16)
<223> OTHER INFORMATION: potential peptide epitope; Xaa is citrulline
      (IUPAC name: 2-amino-5-(carbamoylamino)pentanoic acid)

<400> SEQUENCE: 26

Val Tyr Ala Thr Xaa Ser Ser Ala Val Xaa Leu Xaa Ser Ser Val Pro
1               5                   10                  15

<210> SEQ ID NO 27
<211> LENGTH: 16
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(16)
<223> OTHER INFORMATION: potential peptide epitope; Xaa is citrulline
      (IUPAC name: 2-amino-5-(carbamoylamino)pentanoic acid)

<400> SEQUENCE: 27

Val Tyr Ala Thr Tyr Gly Ser Ala Val Xaa Leu Xaa Ser Ser Val Pro
1               5                   10                  15

<210> SEQ ID NO 28
<211> LENGTH: 16
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(16)
<223> OTHER INFORMATION: potential peptide epitope; Xaa is citrulline
      (IUPAC name: 2-amino-5-(carbamoylamino)pentanoic acid)

<400> SEQUENCE: 28

Val Tyr Ala Thr Xaa Ser Ser Ala Val Gly Leu Gly Ser Ser Val Pro
1               5                   10                  15

<210> SEQ ID NO 29
<211> LENGTH: 16
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(16)
<223> OTHER INFORMATION: potential peptide epitope; Xaa is citrulline
      (IUPAC name: 2-amino-5-(carbamoylamino)pentanoic acid)

<400> SEQUENCE: 29

Ala Xaa Thr Lys Gln Thr Ala Xaa Lys Ser Thr Gly Gly Lys Ala Pro
1               5                   10                  15

<210> SEQ ID NO 30
<211> LENGTH: 16
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(16)
<223> OTHER INFORMATION: potential peptide epitope; Xaa is citrulline
      (IUPAC name: 2-amino-5-(carbamoylamino)pentanoic acid)

<400> SEQUENCE: 30
```

```
Ala Ala Xaa Lys Ser Ala Pro Ser Thr Gly Gly Val Lys Lys Pro His
1               5                   10                  15

<210> SEQ ID NO 31
<211> LENGTH: 17
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(17)
<223> OTHER INFORMATION: potential peptide epitope; Xaa is citrulline
      (IUPAC name: 2-amino-5-(carbamoylamino)pentanoic acid)

<400> SEQUENCE: 31

Tyr Xaa Pro Gly Thr Val Ala Leu Xaa Glu Ile Lys Lys Tyr Gln Lys
1               5                   10                  15

Ser

<210> SEQ ID NO 32
<211> LENGTH: 19
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(19)
<223> OTHER INFORMATION: potential peptide epitope; Xaa is citrulline
      (IUPAC name: 2-amino-5-(carbamoylamino)pentanoic acid)

<400> SEQUENCE: 32

Leu Ile Xaa Lys Leu Pro Phe Gln Xaa Leu Val Xaa Glu Ile Ala Gln
1               5                   10                  15

Asp Phe Lys

<210> SEQ ID NO 33
<211> LENGTH: 16
<212> TYPE: PRT
<213> ORGANISM: Artificial sequence
<220> FEATURE:
<223> OTHER INFORMATION: Synthesized sequence
<220> FEATURE:
<221> NAME/KEY: MISC_FEATURE
<222> LOCATION: (1)..(16)
<223> OTHER INFORMATION: potential peptide epitope; Xaa is citrulline
      (IUPAC name: 2-amino-5-(carbamoylamino)pentanoic acid)

<400> SEQUENCE: 33

Leu Cys Ala Ile His Ala Lys Xaa Val Thr Ile Met Pro Lys Asp Ile
1               5                   10                  15
```

THERAPEUTICS FOR AUTOIMMUNE DISEASE: SYNTHETIC ANTIGENS

CROSS-REFERENCE TO RELATED APPLICATIONS

This application is a national phase application under 35 U.S.C. § 371 of PCT International Application No. PCT/EP2019/052677, filed Feb. 4, 2019, which claims the benefit of European Application No. 18154924.7, filed Feb. 2, 2018, each of which is herein incorporated by reference.

SEQUENCE LISTING

The instant application contains a Sequence Listing which has been submitted electronically in ASCII format and is hereby incorporated by reference in its entirety. Said ASCII copy, created on Dec. 23, 2020, is named 2020-12-23_38659-251-SQL_ST25.txt and is 13,989 bytes in size.

FIELD OF THE INVENTION

The present invention concerns therapeutics for autoimmune diseases and provides a new method for elimination of inflammation causing autoantibodies in humans and animals by application of synthetic antigens presented within a unique nano-conjugate complex forming a therapeutic nanoparticle.

BACKGROUND OF THE INVENTION

Antigen-antibody recognition is the key immune defense in humans that protects us against bacteria, viruses and cancer. However, when having an autoimmune disease, antibodies attack one's own cells and tissue causing inflammation, pain, potential long-term disability, and in some cases death.

Autoimmune conditions develop when the function of the immune system to detect, deflect and destroy the pathogens goes wrong and attacks the subject's own organs, tissues and cells. Approximately 5%-8% of the total human population in the world is affected by autoimmune diseases. The effect of autoimmune diseases depends on the organ affected by it and in systemic autoimmune diseases more than one organ can be affected. Existing therapeutic options for autoimmune diseases are incomplete, and robust tools and techniques for early diagnosis and treatment of autoimmune diseases are on demand.

Treatment of autoimmune disease aims to control the overactive immune response and bring down inflammation. Traditional drugs used to treat these conditions include anti-inflammatory drugs (such as ibuprofen and naproxen) and immune-suppressing drugs. The traditional therapies for autoimmune disease which rely on immunosuppressive medications that globally dampen immune responses are often needed as long-term treatments in high doses to maintain disease control, leaving the patient susceptible to life-threatening opportunistic infections and long-term risk of malignancy. In addition, the benefits of many of these drugs are counterbalanced by toxicity and serious side effect profiles. Thus, there has been a push for the development of more specific strategies that lower the risk of systemic immune suppression and improve tolerability.

Systemic Lupus Erythematosus (SLE)

SLE is a chronic, inflammatory, variable autoimmune disease of connective tissue that occurs chiefly in women and is typically characterized by fever, skin rash, fatigue, and joint pain and often by disorders of the skin, muscles and bone, blood vessels, kidneys, heart, lungs, and brain. The cause of SLE is not clear, but it is thought to involve genetics together with environmental factors. The mechanism involves an immune response by autoantibodies against the subject's own tissues. These are most commonly anti-nuclear antibodies and they result in inflammation. The diagnosis can be difficult and is based on a combination of symptoms and laboratory tests. There are a number of other kinds of lupus erythematosus including discoid lupus erythematosus, neonatal lupus, and subacute cutaneous lupus erythematosus. Unlike rheumatoid arthritis, lupus arthritis is less disabling and usually does not cause severe destruction of the joints.

SLE results in a production of various autoimmune antibodies, with a >40% fraction of antibodies towards nuclear components, i.e. nucleic acid and their binding proteins: DNA, RNA, nuclear proteins histones, RNA polymerase, etc. around 180 auto-antibodies are recognized in SLE patients that attack the antigens of nucleus, cytoplasma, cell membrane, phospholipids, blood cells, nervous system, plasma protein, endothelia cells and matrix proteins. It is believed that debris of apoptotic cells are the main source of auto-antigens in SLE patients. The pathogenesis in SLE is thought to be initiated by aberrant innate system responses resulting in tissue injury by production of inflammatory cytokines and organ injury by aberrant activation of autoreactive T and B cells which lead to production of pathogenic auto-antibodies. Nuclear antigens are released from apoptotic cells and deposited in dendritic cells and T-lymphocytes for presentation to B lymphocytes and T helper cells followed by activation of innate immune cells. Upon the disease progression and increased titers, anti-DNA antibodies and other anti-nuclear antibody (ANA)-activated T and B cells accumulate in the affected part of the body, which may promote further inflammation in multiple organs, and in many cases over time results in Chronic Kidney Disease (CKD). Notably, CKD is the most common cause of lethality in SLE patients. SLE is extremely complicated and challenging as no two cases are the same.

Chronic kidney disease (CKD) is a condition in which there is a progressive and permanent loss of kidney function. CKD caused by SLE (lupus nephritis) happens when autoantibodies produced under SLE reach the kidneys and lead to glomerulonephritis, an inflammation of the kidney's filtering units caused by the autoantibodies being deposited in the glomeruli; or to interstitial nephritis, an inflammation of the kidney's tubules and surrounding structures. Up to 60% of SLE patients will develop lupus nephritis and CKD. Anti-DNA antibodies (ANA) and other ANA are proven to play a major role in the CKD development. When the kidneys are inflamed, they cannot function normally and for example leak protein. If not controlled, lupus nephritis can lead to kidney failure and death [Ehrenstein et al. 1995. Kidney Int. 48(3):705-11; Mason et al. 2001. Clin Exp Immunol. 126(1):137-42.].

CKD caused by autoimmune disease such as SLE is a multifactorial disorder with a strong impact of anti-dsDNA antibodies and other ANA. Nevertheless, antigens produced by immune system genes are among the most conserved genes. Therefore animal models and in particular the lupus mice model has been actively explored to study kidney disease [Yang et al. 2010. Drug Discov Today Dis Models. 7(1-2): 13-19]. Spontaneous mouse models of lupus have led to identification of numerous susceptibility gene regions from which several candidate genes have emerged for therapy. Meanwhile, induced models of lupus have provided insight into the role of environmental factors in lupus pathogenesis and of kidney failure associated with autoimmune antibodies.

Antibodies to nucleic acids are just one part of the complicated autoimmune response taking place in SLE. Especially in SLE, a broad range of antibodies are being produced to nuclear peptides, protein (i.e. histones), and enzymes. Recent studies showed clinical relevance of synthetic analogues of histones in SLE [Muller 2014. Autoantibodies (third edition), chapter 23, p 195-201, ELSEVIER].

Rheumatoid Arthritis (RA)

Today rheumatoid arthritis (RA) is a life-long diagnosis for over 100 million people worldwide. Existing therapies reduce the symptoms of RA, however they do not prevent a physical disability in RA patients. This poses a clear challenge for existing treatment and promotes the development of alternative approaches, e.g. antibodies and synthetic nanomaterials.

Neutrophils are the most abundant white blood cells in humans. Approximately 1011 neutrophils are produced daily which accounts for approximately 50-70% of all leukocytes. Emerging evidence suggests that neutrophils also have a previously unrecognised role in RA [Nature Reviews Rheumatology vol. 10, p. 593-601 (2014)]. For example, citrullinated proteins that can act as neoepitopes in loss of immune tolerance are generated enzymatically within neutrophils. Citrullination of arginine in peptides and proteins has been extensively studied in the last two decades as a biomarker of autoimmune diseases (Front Immunol. 2019 Jan. 4; 9:3033; Arthritis Rheumatol. 2018 December; 70(12):1933-1945; Arthritis Rheumatol. 2019 February; 71(2):210-221).

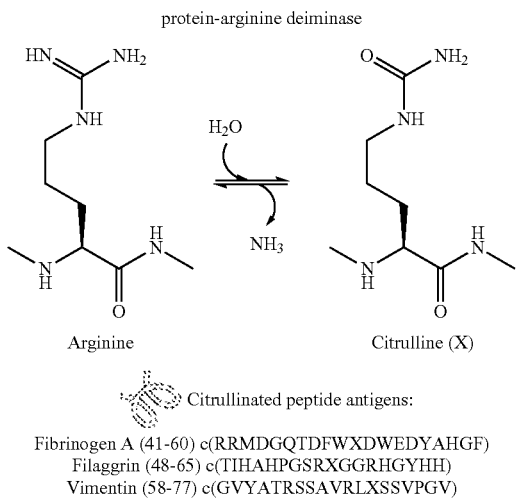

Chemical structure of arginine, citrullin, and examples of citrullinated peptides associated with rheumatoid arthritis.

The most commonly accepted molecular mechanism for citrullinated peptides in RA is that the modified antigen resulting from cell damage or uncontrolled apoptosis could evoke an immune response leading to autoantibodies against these peptide or the whole protein. Autoreactive antibodies to citrullinated peptides (ACPA) are associated with RA. ACPA recognize a variety of citrullinated antigens—prominent among them being citrullinated α-enolase, vimentin, type II collagen, fibrinogen and histone. Notably, ACPA can be detected years before the onset of RA and are predictive of a severe disease. This has made citrullinate peptides an exciting object of studies for targeted drug delivery and a valuable diagnostic tool.

Aiming at diagnostic and therapeutic applications, peptide libraries have been developed for discovery of better citrullinated epitopes. Over the last decade, 2nd generation cyclic citrullinated peptide (CCP2) and 3rd generation cyclic citrullinated peptide (CCP3) assays have been developed. Apart from the main difference in epitope, both CCP2 and CCP3 use enzyme-linked immunosorbent assay (ELISA) method. Most studies, however, show no evident improvement of CCP3 compared to CCP2 assays.

Psoriasis Arthritis (PsA)

Psoriatic arthritis (PsA) is a chronic inflammatory disease in which arthritis is associated in most cases with psoriasis. The biological and clinical spectrum of PsA may present common elements with rheumatoid arthritis (e.g. symmetrical arthritis of the hands, elevated acute phase proteins) or with the general class of spondylarthropathies (e.g. dactylitis, enthesitis, sacroiliitis). As another common feature, anti-cyclic citrullinated peptide (CCP) antibodies are detectable in blood samples not only in patient with RA, but also in patients with PsA.

Type I Diabetes (T1D)

Type 1 diabetes mellitus is an autoimmune disorder characterized by the cellular-mediated autoimmune destruction of β cells of the pancreas, causing to insulin deficiency. The development of T1D is faster than other type of diabetes and it is usually diagnosed in young adults, adolescents and children. The exact cause of T1D is still unknown and it is still not preventable. However, it is agreed that T1D is the result of interaction of genetic and environmental factors. The majority T1D is cell mediated autoimmune attack of T cell causing the loss of β cells and partial and complete production of insulin. It is estimated that approximately 5%-10% cases of diabetes mellitus are T1D. The patients with T1D should have insulin medication regularly to maintain the amount of glucose level in their blood to survive. Different autoantibodies like insulin autoantibody and glutamic acid decarboxylase autoantibody can manifest autoimmune response. Inflammation of endocrine tissues in pancreas with destruction of β cells causes pre-diabetes and diabetes mellitus. Furthermore, the patients are prone to other autoimmune diseases as well, such as Gravis, Addison's disease, Celiac disease etc. The genome wide association study and meta-analysis shows that around 40 genetic loci are associated with T1D, where the loci in the major histocompatibility region have more chances to develop T1D. Different theories have been proposed in the last few years to explain the 1 cell-mediated autoimmunity including molecular mimicry, loss of tolerance and cytokine induced damage.

Multiple Sclerosis (MS)

MS is a demyelinating disease in which the insulating covers of nerve cells in the brain and spinal cord are damaged. [1] This damage disrupts the ability of parts of the nervous system to communicate, resulting in a range of signs and symptoms, including physical, mental, and sometimes psychiatric problems. MS is the most common immune-mediated disorder affecting the central nervous system.

Scleroderma

Scleroderma is a chronic disease characterized by skin fibrosis and is divided into two clinical entities: localized scleroderma and systemic sclerosis. It is recognized that autoimmune antibodies are involved in the diseases.

Nanoparticles (NP) Nanoparticles like polymeric nanoparticles, microspheres, viral nanoparticles, silica nanoparticles, liposomes, polysaccharides, dendrimers and carbon nanotubes are widely used to deliver drugs at the right site of interest. The poor stability and less specificity of liposomes and polydisperse nature of polymers decreased the focus of liposomes and polymeric systems. However, dendrimers and polysaccharides have potential to be used in novel strategies for nano-therapeutics techniques.

The globular hyperbranched architecture of dendrimers with multivalent surfaces containing active sites and a core with attached dendrons in dendrimers allow wide range of modification in it which makes it one of the novel approach in biology, nanotechnology and medicine for therapeutics. The number of branching points from a central core molecule (ammonia, ethylenediamine and polydiamine or benzene tricarboxylic acid chloride) determines the length and generation of dendrimers which can reach to nanometres, and can be used as the precisely engineered macromolecules (Kesharwani, et al. Progress in Polymer Science, Vo. 39 (2014) p. 268-307). Different dendrimers like PAMAM (Poly amido amine), PPI (Polypropyleneimine), DAB (Diaminobutyl), Phosphorous based dendrimers, Carbosilane dendrimers, polylysine dendrimers and new class of dendrimer called Janus dendrimers have attracted much attention due to their outstanding properties in conjugating multiple drugs and targeting moieties, enabling delivery system and drug encapsulation. Among the widespread family of dendrimers, PAMAM is most well-characterized and first to commercialize as it has better biocompatibility than other dendrimer families. PAMAM has well-defined structure with numerous branches including active amine groups on the surface which increase the solubility of various drugs. The unique property of PAMAM like globular protein and the cost-effective synthesis along with its functionality made it one of the promising candidates in drug development, nanotechnology and therapeutics.

PAMAM

Poly(amidoamine) dendrimer (PAMAM) holds a strong position in various biomedical application with its ethylenediamine core and the branches consisting methyl acrylate and ethylenediamine. The number of amino groups on the surface of PAMAM dendrimers increases exponentially from 4 to 128 and generation size from G0 to G5 (FIG. 1) and the functional amino group can be used to engineer the dendrimer for drug delivery in specific targets. Despite numerous applicability with their well-defined properties in various drug delivery applications, dendrimers have certain limitation including rapid systemic clearance and toxicity with its cationic groups and difficulty in drug release. The presence of large number of amino groups and carboxyl groups cause strong interaction between the cationic PAMAM and anionic cell membrane causing membrane disruption and toxicity which is major hurdle in its use. Surface modification of positively charged PAMAM is the possible solution to overcome these drawbacks. The surface of dendrimers is modified to reduce toxicity, enhance encapsulation and improve biocompatibility without affecting its drug delivery capacity. Different strategies are proposed for neutralizing the cationic groups of PAMAM dendrimer by neutral or anionic groups such as PEGylation, acetylation, carbohydrate conjugation, peptide conjugation, DNA/gene conjugation, neutral hydroxyl, acetyl or negatively charged carboxyl groups, antibody conjugation, folate conjugation and miscellaneous. Among these possibilities, Polyethylene Glycol (PEG) is widely used to conjugate with PAMAM dendrimer. PEG is inert, non-immunogenic and non-antigenic molecules and PEGylation is one of the most effective and easiest approaches. The PEGylated PAMAM drug delivery system helps to overcome the aforementioned limitations of dendrimers and the significant water solubility of PEG molecules improve the solubilization of hydrophobic drugs and improves the ability of drug delivery system (Luong et al. Acta Biomaterialia, Vol. 43 (2016) p. 14-29).

Chitosan

Chitosan (CS) is a natural occurring water-soluble and a bioadhesive linear polysaccharide composed of randomly distributed β-(1→4)-linked D-glucosamine (deacetylated unit) and N-acetyl-D-glucosamine (acetylated unit). Hyaluronic acid (HA) is an anionic, nonsulfated glycosaminoglycan distributed widely throughout connective, epithelial, and neural tissues. Chitosan/hyaluronic acid conjugate (CS-HA) nanoparticles have been shown to be able to deliver an RNA/DNA cargo to cells overexpressing HA receptors such as CD44 (Lallana et al. Mol Pharm. Vol. 14 (2017) p. 2422-2436).

PRIOR ART

US2015118183 discloses a pharmaceutical composition including (e.g., for use as an adjuvant) a (negatively charged) nucleic acid comprising complex comprising as a carrier cationic or polycationic compounds (e.g. peptides, proteins or polymers) and as a cargo at least one nucleic acid (molecule) and at least one antigen that is selected from an antigen from a pathogen associated with infectious disease; an antigen associated with allergy or allergic disease; an antigen associated with autoimmune disease; or an antigen associated with a cancer or tumour disease. The pharmaceutical composition allows for induction of an adaptive immune response directed against said antigen.

U.S. Pat. No. 9,744,241 discloses gene therapy, such as gene silencing by use of a hyaluronic acid-nucleic acid complex.

WO 07/100699 discloses immunogenic compositions which comprise microparticles that further comprise a biodegradable polymer. The microparticle compositions also comprise a cationic polysaccharide and an immunological species selected from an antigen, an immunological adjuvant and a combination thereof.

WO 12/024530 discloses particles, which can be used, for example, in the delivery of a therapeutic peptide or protein, for example, in the treatment of cancer, inflammatory disorders, autoimmune disorders, cardiovascular diseases, or other disorders. The particles, in general, include a hydrophilic-hydrophobic polymer (e.g., a di-block or tri-block copolymer) and a therapeutic peptide or protein. In some embodiments, the particle also includes a hydrophobic polymer or a surfactant. In general, the therapeutic peptide is attached to a polymer, for example a hydrophilic-hydrophobic polymer, or if present, a hydrophobic polymer

SUMMARY OF THE INVENTION

The present invention addresses the unmet need in the direct treatment of autoimmune diseases by targeting and removing inflammatory autoantibodies from the circulatory system in humans and animals with autoimmune diseases. Specifically, autoantibodies to self-DNA and-peptides that are involved in the cause and progression of autoimmune diseases are targeted by the present nanoparticles consisting of unique nanoconjugate complexes. The approach is not limited to a certain sub-type of antibody; all classes involved in autoimmune response (IgG, IgM and IgA) may be targeted and removed.

As a general principle, the present invention provides nanoconjugate complexes comprising autoimmune-specific antigens presented on the surface of functionalized soluble nanoparticles. The nanoparticles may according to the present invention be decorated with different helper moieties adding functionalities to the conjugate for displaying the desired properties, such as size, solubility and transport to particular organs for subsequent clearance etc.

An important property of the nanoconjugates of the present invention is that it is not in itself toxic to the patient. The use of nano sized particles of about 100 to about 500 nm together with blockage of charged surface groups secure a very limited uptake of the particles over cell membranes and thus reduced toxicity. Another important property is that the nanoconjugates, including the used autoantibody-specific antigens, are not antigenic in the patient per se. This achieved by the particle quenching any induction or maintenance of (auto)immune reactions by the conjugated and partly buried auto-antigen or auto-antigen mimic.

In its broadest aspect the present invention provides a nanoconjugate complex comprising the following components:
  i. at least one specific antigen recognized by autoantibodies related to an autoimmune disease,
  ii. at least one helper agent/moiety, and
  iii. a nanoparticle carrier for the components i and ii,
  wherein each of the components i and ii independently is the same component or different components.

In one embodiment of the present invention there is provided a nanoconjugate complex, wherein the antigen or antigens and the helper moiety or moieties are independently linked directly to the nanoparticle carrier by covalent and/or non-covalent bindings.

The nanojugate complex may be illustrated by the following general structures GS:

$$\boxed{H}\!-\!\underset{n_h}{\overset{Lh}{\boxed{\phantom{x}}}}\!-\!\boxed{A}\!-\!\underset{n_d}{\overset{Ld}{\boxed{\phantom{x}}}}\!-\!\boxed{D}$$

wherein A is a nanoparticlular carrier to which $n_d$ disease-specific antigen moieties (D) and $n_h$ surface modifying helper moieties (H) are attached through direct links or linkers Ld and Lh, respectively; $n_d$ and $n_h$ are independent integers between 1 and N−1 and wherein the sum of $n_d$ and $n_h$ is between 2 and the total number of surface groups N available on A for covalent or non-covalent attachment; and wherein H is one or more different surface modifying helper moieties.

In another embodiment of the present invention there is provided a nanoconjugate complex, wherein the antigen or antigens is/are linked to a helper moiety H1 by covalent or non-covalent binding and optionally other helper moieties H2 are independently linked directly to the nanoparticle carrier and/or via the helper moiety H1 by covalent or non-covalent binding.

In this embodiment, D is linked to A via a helper moiety H/H1. A optionally comprises $n_{h2}$ other helper moieties H2 without D linked directly to A by Lh. The number of D on each H1 ($n_{d1}$) is between 0 and the available binding groups on H1 for conjugated or non-conjugated binding to D. The nanoconjugate complex will comprise at least one D. H1 may attach further $n_{h3}$ helper moieties H2 via a link/linker Lh.

$$\boxed{D}\!-\!\underset{n_d}{\overset{Ld}{\boxed{\phantom{x}}}}\!-\!\boxed{H}\!-\!\underset{n_h}{\overset{Lh}{\boxed{\phantom{x}}}}\!-\!\boxed{A}$$

$$\boxed{D}\!-\!\underset{n_{d1}}{\overset{Ld}{\boxed{\phantom{x}}}}\!-\!\boxed{H1}\!-\!\underset{n_{h1}}{\overset{Lh}{\boxed{\phantom{x}}}}\!-\!\boxed{A}\!-\!\underset{n_{h2}}{\overset{Lh}{\boxed{\phantom{x}}}}\!-\!\boxed{H2}$$
$$\underset{n_{h3}}{\overset{Lh}{\big|}}$$
$$\boxed{H2}$$

The nanoconjugate complex of this aspect of the present invention consists of a complex of different functionalities H and D collected on the surface of the carrier A which ensures that the nanoconjugate complex is soluble in the blood stream, too big to pass cell membranes, presents at least one antigen (in a protected way for not being immunogenic), and is tolerable (non-toxic and non-immunogenic) to the subject/patient.

In a preferred embodiment, A is a polysaccharide, such as chitosan or pullulan; or a polypeptide such as silk fibroin or human serum albumin and H/H1 is a polysaccharide such as hyaluronic acid (HA); or a polymer, such as polyethylene glycol, or a conjugate of two or more different H, such as PEGulated HA.

In another particular aspect the present invention provides a nanoconjugate complex comprising the following components:
  i. at least one specific antigen recognized by autoantibodies related to an autoimmune disease,
  ii. at least one carbohydrate moiety,
  iii. at least one lipid moiety,
  iv. at least one polymer moiety, and
  v. a nanoparticle carrier for the components i, ii, iii and iv
  where each of the individually components i, ii, iii and iv independently are the same component or different components.

The nanoconjugate complex may be illustrated by the following general structure II:

II $$\boxed{C}$$
$$\underset{n_c}{\overset{Lc}{\big|}}$$
$$\boxed{B}\!-\!\underset{n_b}{\overset{Lb}{\boxed{\phantom{x}}}}\!-\!\boxed{A}\!-\!\underset{n_d}{\overset{Ld}{\boxed{\phantom{x}}}}\!-\!\boxed{D}$$
$$\underset{n_e}{\overset{Le}{\big|}}$$
$$\boxed{E}$$

wherein A is a nanopolymeric carrier to which $n_b$ lipid moieties (B), $n_c$ carbohydrate moieties (C), $n_d$ disease-specific antigen moieties (D), and $n_e$ polymer moieties (E) are attached through direct links or linkers Lb, Lc, Ld, and Le, respectively; $n_d$ is at least 1 and $n_b$, $n_c$ and $n_e$ are independent integers between 1 and X−3 and wherein the sum of $n_d+n_c+n_d+n_e$ is between 4 and the total number of surface groups X available on A for covalent or non-covalent attachment.

In a preferred embodiment, A is a synthetic polymer, such as PAMAM, PNIMAM etc. In another embodiment, A is a natural polymer, such as chitosan.

A is a nanoparticle and carrier (transporter) of the antigen(s) and one or more different other functionalities. It is of nano size for optimal transport and long survival in the cardiovascular system, preferably in globular form with many active sites on the surface and preferably an organic polymer, either a natural organic polymer, or a synthetic organic polymer. The nanoparticle may also be an inorganic particle such as silica or gold or other suitable inorganic carriers.

Natural organic polymers are known in the art and comprise polysaccharides such as chitosan and pullulan, etc.; polypeptides such as silk fibroin and human serum albumin, etc.; liposomes, lipoplexes; or polymeric micelles of various chemical compositions.

Synthetic organic polymers are known in the art and comprise dendrimers and similar carbon-based polymeric structures. Dendrimers have a three dimensional, hyperbranched globular nanopolymeric architecture, which have immense potential over other carrier systems in the field of drug delivery. It consists of three structural units, a core, branching units and a number of terminal end groups. The end groups (surface groups) may possess positive, negative or neutral charges, which are vital for use in drug transport and delivery. Each layer of branching units added to the growing polymer is called a "generation" and many dendrimers have been produced in up 7 or 8 generations (G0, G1, G2, G3, G4, etc.). Cationic dendrimers, such as poly-L-lysine, poly(propyleneimine) (PPI), linear or branched poly(ethyleneimine) (PEI), bis-MPA-azide dendrimer, poly (amidoamine) (PAMAM), can form complexes with negatively charged DNA and the positively charge on the dendrimers will facilitate interaction with negatively charged molecules and structures such as biological cell membranes leading to the dendrimers being capable of delivering DNA and drug intracellularly. Cell membrane interaction may, however, lead to cytotoxicity, hemolysis etc. Such negative properties may be overcome by surface modifications of the dendrimers with different agents such as carbohydrates, PEG, acetate etc. (Kesharwani et al. Progress in Polymer Science, Vol. 39 (2014) pp. 268-307; Luong et al., Acta Biomaterialia, Vol. 43 (2016) pp. 14-29). Carbosilane dendrimers are anionic. Dendrimers are synthesized by either divergent or convergent approaches and formed. A example of an anionic polymer is poly(methacrylic acid) (PMAA). Poly(N-isopropylacrylamide) (PNIPA) is a polymer being water soluble at low temperatures but non-polar at higher temperatures.

B is one or more different lipids which ensure the nanoparticle is targeting the right target tissue for clearance and/or phagocytosis. Examples of lipids are fatty acids selected from fatty acids containing straight or branched chains with a chain length of 7 or more carbon atoms. In a preferred embodiment, the lipid is one or more fatty acids selected from caproic (hexanoic) acid, enanthic (heptanoic) or acidenanthic (heptanoic) acid, caprylic acid, pelargonic acid, capric acid, undecylic acid, lauric acid, tridecylic acid, myristic acid, pentadecylic acid and palmitic acid. Preferably B is a single lipid, such as hexanoic acid or heptanoic acid.

C is one or more different carbohydrates which increase the solubility of the complex, especially when lipids are attached, for prolonging the time being present in the blood stream and which helps the complex in reaching the target tissue for clearance and/or phagocytosis. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a polysaccharide, including but not limited to pullulan, cellulose, macrocrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, carboxylmethylchitosan, algin and alginic acid, starch, chitin, inulin, konjac, glucomannan, pustulan, heparin, hyaluronic acid, curdlan, and xanthan. Preferred examples are mannose, galactose, glucosamine, and their oligomers. In a preferred embodiment, the carbohydrate is selected from galactose, glucosamine and mannose.

D is one or more autoimmune disease-specific antigen(s), selected from peptides, oligonucleotides and phospholipids.

E is one or more different polymers which, together with the carbohydrate moieties if present, ensure solubility and stability of the complex in the cardiovascular system. Important properties of the polymers are to "block" at least some of the charged surface groups on the nanoparticle carrier and to prevent the nanoparticle complex from crossing cell membranes such that the circulation time is increased in the blood stream preferably until the nanoparticle is cleared. Examples of polymers are polysaccharides, such as chitosan or pullulan (a water-soluble polysaccharide polymer consisting of maltotriose units, also known as $\alpha$-1,4-;$\alpha$-1,6-glucans'); glycosaminoglycans, such as hyaluronic acid, an anionic, nonsulfated glycosaminoglycan, belonging to the group of highly polar long unbranched polysaccharides consisting of a repeating disaccharide unit consisting of an amino sugar (N-acetylglucosamine or N-acetylgalactosamine) along with a uronic sugar (glucuronic acid or iduronic acid) or galactose; polypeptides such as silk fibroin or human serum albumin; polyalkylene glycol or polyethylene glycol (PEG), etc. In cases where the polymer itself contains functional surface groups, these can be blocked by use of an "inert" blocking group, such as for example PEG, or inactivated chemically (e.g. by deacetylation). The polymer may also be cross-linked by use of cross-linkers known in the art if needed for creating a globular polymeric structure or architecture and/or for inactivating functional surface groups.

In one embodiment of the present invention, the specific antigen(s) of the nanoconjugate complex is/are the same or different and selected from a peptide and an oligonucleotide related to SLE and in particular the autoimmune kidney disease CKD. In a preferred embodiment, the specific antigen(s) is/are selected from SEQ ID NO. 1, SEQ ID NO. 2, SEQ ID NO. 3, SEQ ID NO. 4, SEQ ID NO. 5, and SEQ ID NO. 6.

In another embodiment of the present invention, the specific antigen(s) of the nanoconjugate complex is/are the same or different and selected from a peptide and an oligonucleotide related to RA, rheumatoid arthritis. In a preferred embodiment, the specific antigen is SEQ ID NO. 10.

In a further embodiment, the links or linkers connecting the antigen(s) and the other surface substituents to the nanoparticle carrier of the nanoconjugate complex are the same or different, consisting of one or more functional group(s) selected from ether, ester, disulfide, amide, 1,2,3-triazole, PEG, and electrostatic interaction. In a preferred embodiment, one or more of the substituent are linked to the carrier by way of click chemistry which is a common known technique for covalent coupling of two compounds.

In an alternative structure of the nanoconjugate, two, three or four of the B, C, D and E units can be linked together in a single unit and further linked to the backbone carrier A.

Another aspect of the invention provides a method for preparing nanoconjugate complexes of the present invention, comprising the steps:
a. providing a nanoparticle carrier for use in connecting all the components of the nanoconjugate complex as set forth in steps b-e in any order,
b. linking at least one polymer component to the carrier
c. linking at least one specific antigen component to the carrier
d. optionally linking at least one lipid component to the carrier
e. optionally linking at least one carbohydrate component to the carrier.

The nanoconjugate complexes of the present invention may be used in treating autoimmune diseases. Autoimmune diseases are selected from any autoimmune disease where antigens are or can be identified for use in the complex. Examples of autoimmune diseases are SLE, including CKD; RA; T1D; psoriasis; vasculitis; inflammatory bowel disease (IBD), including ulcerative colitis and Crohn's disease; multiple sclerosis (MS); Guillain-Barre syndrome; Graves' disease; Hashimoto's thyroiditis and Myasthenia gravis.

In an aspect of the invention there is provided a pharmaceutical composition comprising a nanoconjugate complex together with pharmaceutically acceptable additives or excipients as well as a method for treatment of an autoimmune kidney disease in a patient, comprising the steps.

A method of treatment of an autoimmune kidney disease, comprising the steps:
a. Providing a nanoconjugate complex or a pharmaceutical composition according to the present invention comprising antigen(s) associated with an autoimmune disease; and
b. Administering said nanoconjugate complex or said pharmaceutical composition to a patient suffering from said autoimmune disease.

DETAILED DESCRIPTION OF THE INVENTION

Definitions

Figure 1:
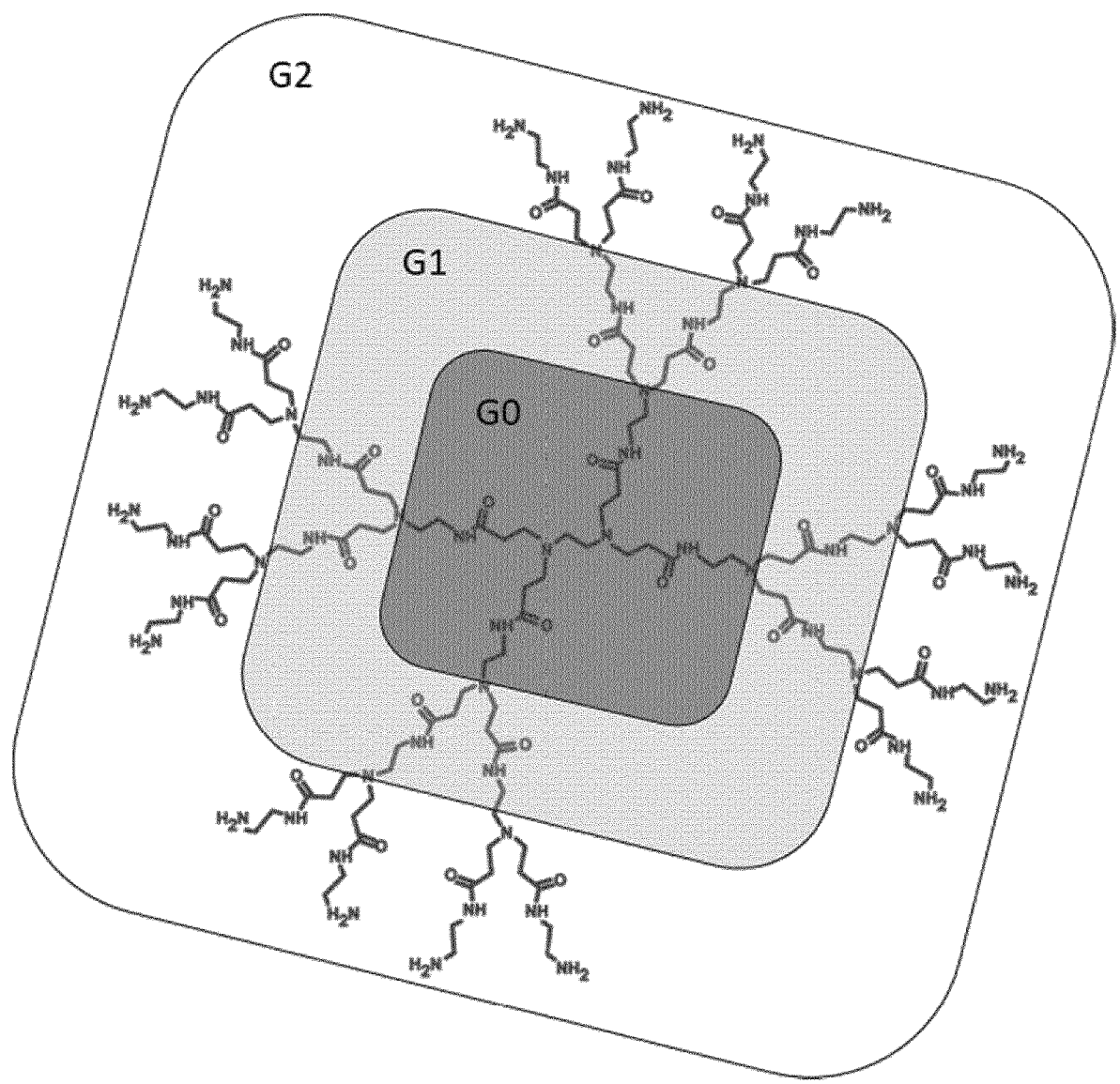
FIG. 1. Structure of PAMAM, illustrating exponential branching of G0, G1, and G2

"Autoimmune disease" is a condition in which the immune system produces autoantibodies that instead of fighting infections, attack the body's own tissues.

The term "autoimmune kidney disease" as used herein means chronic kidney disease caused by autoantibodies "CKD" means chronic kidney disease, which is a condition in which there is a progressive loss of kidney function.

"SLE" means systemic lupus erythematosus; which is an example of an autoimmune disease that may cause CKD.

"T1D" means type 1 diabetes, which is another example of an autoimmune disease that may cause CKD.

"RA" means rheumatoid arthritis

"MS" means Multiple Sclerosis

"Autoantibody" is an antibody produced by the immune system directed against the individual's own tissues.

"ANA" means anti-nuclear antibodies which are autoantibodies that bind to contents of the cell nucleus.

"Anti-dsDNA (a-ds-DNA) antibodies" are a group of ANA, the target antigen of which is double stranded DNA.

"Anti-histone antibodies" are autoantibodies that are a subset of ANA; they target protein components of nucleosomes, the DNA-protein complexes that form the substructure of transcriptionally inactive chromatin.

The term "nanoconjugate complex" (also just referred to as "nanoconjugates" or simply "conjugates", or nanocarrier complex) as used herein, defines as a molecule comprising at least one specific antigen, at least one helper moiety, and a nanoparticle carrier. Such nanoconjugate complex may comprise (i) at least one antigen, (ii) at least one carbohydrate, (iii) at least one lipid, (iv) at least one polymer, and (v) a backbone connecting components i, ii, iii and iv. One nanoconjugate complex may comprise more than one of each of the antigen and helper moiety components if desired, the only limitation being the number of available surface groups/functional groups in the backbone for attachment of the components.

The term "backbone" as used herein, is a molecule that connects components of the nanoconjugate complex. It is also referred to as nanoparticle carrier or simply nanocarrier. The backbone functions as a carrier and transporter of the antigen or antigens in the cardiovascular system.

The term "helper moiety" broadly refers to molecules which help ensure the functionality of the nanoconjugate complex of clearing autoantibodies from the blood-stream, such as e.g. by contributing to solubility of the complex in the blood stream and ensuring the complex will not pass across the cell membranes.

The term "attachment site" as used herein, means sites on the backbone where the different components (antigen(s), carbohydrate(s), lipid(s), polymer(s)) of the nanoconjugate complex may be attached to the backbone by links or linkers.

"PAMAM" poly(amidoamine) is an example of a backbone component. It is a class of dendrimers made of repetitively branched subunits of amide and amine functionality. PAMAMs have a sphere-like shape overall, and are typified by an internal molecular architecture consisting of tree-like branching, with each outward 'layer', or generation, containing exponentially more branching points and possible functional groups.

The term "HSA" means human serum albumin, which is the serum albumin found in human blood.

"Antigen" is a structural molecule that binds specifically to an antibody. In the present invention, the antigens are recognized by autoantibodies, such as autoantibodies present in patients with SLE-related diseases, CKD, RA, psoriasis, T1D, scleroderma and MS. Antigens as used herein may be peptides, proteins, oligonucleotides, combinations and chemical analogues thereof.

The term "peptides" as used herein, means chains of amino acid monomers lined by peptide bonds with no distinct limitation on chain length.

The terms polypeptide and protein are used interchangeable herein.

The terms "polynucleotide" and "oligonucleotide" are used interchangeable herein, with no distinct limitation on chain length. Polynucleotide is a chain of nucleic acids, such as a DNA or RNA sequence. The term "sequence identity" as used herein, indicates a quantitative measure of the degree of homology between two sequences of substantially equal length, such as two amino acid sequences or two nucleic acid sequences. The two sequences to be compared must be aligned to give a best possible fit, by means of the insertion of gaps or alternatively, truncation at the ends of the protein sequences. The sequence identity can be calculated as ((Nref−Ndif)100)/(Nref), wherein Ndif is the total number of non-identical residues in the two sequences when aligned and wherein Nref is the number of residues in one of the sequences. Sequence identity can alternatively be calculated by the BLAST program e.g. the BLASTP program (Pearson W. R and D. J. Lipman (1988)) (www.ncbi.nlm.nih.gov/cgi-bin/BLAST). Alignment may be performed with sequence alignment methods such as ClustalW with default parameters as described by Thompson J., et al 1994, available at http://www2.ebi.ac.uk/clustalw/.

The term "carbohydrate" as used herein, means a saccharide as well as saccharide derivatives such as amino sugars. The saccharide may be a mono-, di-, poly-, or oligosaccharide.

The term "lipid" as used herein, means fatty acid, a straight or branched aliphatic chain with no distinct limitation of number of carbon atoms.

In the present context the term "polymer" as a component of the nanoconjugate complex means a bulky molecule of a certain size that ensures stability of the nanoconjugate complex in biofluids as well as antigen representation to the autoantibodies.

"PEG" means polyethylene glycol, a polyether compound. PEGs are prepared by polymerization of ethylene oxide and comprise a wide range of molecules with the common formula $C_{2n}H_{4n+2}O_{n+1}$, where n may range from 1 to 1000 or even greater.

The term "links" or "linkers" are used interchangeable herein, and indicates the connection between the backbone of the nanoconjugate complex and the antigen, carbohydrate, lipid and polymer components. More specifically, the linkers may comprise one or more functional group(s) selected from ether, ester, disulfide, amide, 1,2,3-triazole, or PEG. Covalent links made be formed by click chemistry.

Alternatively, the link may be noncovalent, such as an electrostatic interaction.

"Pyrogenicity" is the capacity to produce fever.

The present invention concerns therapeutics for autoimmune diseases caused by autoantibodies in a subject, such as a human or an animal such as a dog, a cat, a horse, etc. In order to target the disease in the most efficient manner, a multicomponent principle is applied. This means that each component of the therapeutic nanoconjugate complex disclosed in the present invention has a specific function.

The present invention concerns therapeutics for treatment of autoimmune diseases selected from different manifestations of SLE, including CKD caused by autoantibodies, alternatively referred to as autoimmune kidney disease in the present context, RA, T1D, Psoriasis, Sclerosis, Sjögren's Symptom, etc.

1. A Nanoconjugate Complex

A first aspect of the present invention provides a nanoconjugate complex comprising the following components:
  i. at least one specific antigen recognized by autoantibodies related to an autoimmune disease,
  ii. at least one helper moiety,
  iii. a nanoparticle carrier connecting components I and ii.

In one embodiment of the aspect, the nanoconjugate complex comprises the following components:
  i. at least one specific antigen recognized by autoantibodies related to an autoimmune disease,
  ii. at least one carbohydrate,
  iii. at least one lipid,
  iv. at least one polymer, and
  v. a backbone connecting components i, ii, iii and iv.

The at least one of components (i), (ii), (iii) and (iv) means at least one of these helper moieties per carrier A. If a helper moiety is present on a carrier in more than one copy, all copies may be the same or different. The different helper moieties are preferably present on a carrier independently in between 4 and 20 copies In one preferred embodiment, the nanoconjugate complex has the following general structure II:

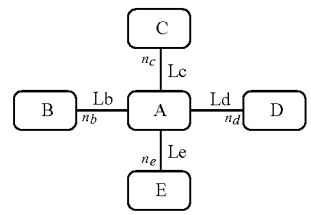

wherein A is a nanopolymeric carrier to which $n_b$ lipid moieties (B), $n_c$ carbohydrate moieties (C), $n_d$ disease-specific antigen moieties (D), and $n_e$ polymer moieties (E) are attached through direct links or linkers Lb, Lc, Ld, and Le, respectively; $n_d$ is at least 1 and $n_b$, $n_c$ and $n_e$ are independent integers between 1 and X−3 and wherein the sum of $n_a+n_c+n_d+n_e$ is between 4 and the total number of surface groups X available on A for covalent or non-covalent attachment.

The nanoconjugate complex of this aspect of the present invention consists of a complex of different functionalities B, C, D and E collected on the surface of the carrier A which ensures that the nanoconjugate complex is soluble in the blood stream, large enough for not passing cell membranes, presents at least one antigen (in a protected way), and is tolerable (non-toxic and non-immunogenic) to the subject/patient.

In a preferred embodiment, A is a synthetic polymer, such as PAMAM, PNIMAM etc.

The nanoconjugate complex may comprise at least one B per backbone (A), i.e. one or more B per A. If B is present on A in more than one copy, all copies of B may be the same or different. The nanoconjugate complex may comprise at least one C per A, i.e. one or more C per A. If C is present on A in more than one copy, all copies of C may be the same or different. The nanoconjugate complex may comprise at least one D per A, i.e. one or more D per A. If D is present on A in more than one copy, all copies of D may be the same or different. The nanoconjugate complex may comprise at least one E per A, i.e. one or more E per A. If E is present on A in more than one copy, all copies of E may preferably be the same. The numbers of B, C, D, and E on A are mutual independent. The number of B, C, D, and E is only limited by the number of "available attachment sites" on A, as described in greater detail in the following section concerning the nanocarrier of the nanoconjugate complex.

In an alternative embodiment, B may be coupled to C and/or D and/or E; C may be coupled to B and/or D and/or E; D may be coupled to B and/or C and/or E; and E may be coupled to B and/or C and/or D; and linked to A.

The location on the backbone of the different components of the nanoconjugate complex with respect to one another may be any physically/chemically possible constellation and should not be limited to the layout illustrated in the general structures above.

1.1 Backbone of the Nanoconjugate Complex, the Nanoparticle Carrier

The backbone of the nanoconjugate complex is a molecule that connects all the components of the complex. Depending on the choice of backbone, the number of available attachment sites for the components may differ.

Different dendrimers may be engineered as candidates for therapeutic application. Dendrimers are repetitively branched molecules which are typically symmetric around the core, and often adopt a spherical three-dimensional morphology. One example is Bis-MPA azide dendrimer, a hyperbranched nanoparticle based on the 2,2-bis(hydroxymethyl)propionic acid (bis-MPA) monomer unit. The azide architecture of this dendrimer can easily be functionalized using click chemistry, which is a well-known method for the synthesis of dendrimers. Applying Bis-MPA azide dendrimer as backbone in the nanoconjugate complexes of the present invention, the azide-branches represent available attachment sites for the antigen(s), carbohydrate(s), lipid(s), and polymer(s) components.

Another dendrimer: poly amido amide (PAMAM) dendrimer has large number of amino and carboxyl groups which may represent available attachment sites for the antigen(s), carbohydrate(s), lipid(s), and polymer(s) components of the nanoconjugate complex of the present invention. PAMAMs have a sphere-like shape overall, and are typified by an internal molecular architecture consisting of tree-like branching, with each outward 'layer', or generation, containing exponentially more branching points. As shown in FIG. 1, dendrimers are "grown" off a central core in an iterative manufacturing process, with each subsequent step representing a new "generation" (G) of dendrimer, e.g. G0 has 4 surface groups, G1 has 8 surface groups, G2 has 16 surface groups, G3 has 32 surface groups, G4 has 64 surface groups, G5 has 128 surface groups, etc, These surface groups represent available attachment sites for the antigen, carbohydrate, lipid, and polymer components. The surface groups may be modified prior or attachment of the components, such as to provide hyrdroxy surface PAMAM, succinamic acid surface PAMAM, sodium carboxylate surface PAMAM, hydrophobe substituted PAMAM, or other surface groups. The functionality of PAMAMs is readily tailored, and their uniformity, size and highly reactive "molecular Velcro" surfaces are the functional keys to their use. PAMAM dendrimers have been used for delivery of genetic material in cell lines and are designed to minimize immune response and cytotoxicity. For this, different modification mechanism of the dendrimers like PEGylation, acetylation, carbohydrate conjugation, peptide conjugation, DNA/gene conjugation, neutral hydroxyl, acetyl or negatively charged carboxyl groups, antibody conjugation, folate conjugation have been proposed.

It is crucial that the backbone does not induce toxicity. Based on the literature [Ayatollahi S, et al. Int J Biochem Cell Biol. 2017 November; 92:210-217], PAMAM and similar scaffold molecules are safe in terms of toxicity and can be applied as backbone for the nanoconjugate complex of the present invention. Other useful backbone units will be apparent for the skilled person.

In one embodiment, the backbone of the nanoconjugate complex is a dendrimer, such as a scaffold molecule selected from PAMAM or bis-MPA-azide dendrimer of any generation size. In another embodiment, the backbone of the nanoconjugate complex is selected from a carbohydrate such as chitosan and pullulan, or a biomolecule such as silk fibroin, or polyethyleneimine, poly(N-isopropylacrylamide), and poly(methacrylic acid). In a preferred embodiment, the backbone of the nanoconjugate complex is PAMAM.

Based on the structure of the backbone, multiple sites may available for the components of the nanoconjugate complex of the present invention to attach to. All available attachment sites on the backbone of the nanoconjugate complex may or may not have functional components attached, such as a specific antigen (D), a lipid (C), a carbohydrate (A), and a polymer component (E) attached. For example, for G5-PAMAM, it may be that only 25-30% of all the termini (branches) are modified with a functional component. However, less termini branches (active sites) may be modified, such as about 5%, about 10%, about 15% or about 20%; or more termini branches are modified, such as about 40%, about 50%, about 60%, about 70%, about 80%, about 90% and up to 100%. Structure I should therefore be regarded merely as an illustration that the nanoconjugate complex comprises a specific antigen (D), a lipid (C), a carbohydrate (A), and a polymer component (E), but not be regarded as limited to one of each component. The nanoconjugate complex may comprise one or more of each component. The ratio of the components is not restricted to 1:1, but may vary. The different components may be mixed and attached randomly throughout the branched backbone; or their location may specifically be preselected.

In another preferred embodiment or the present invention, the nanoconjugate complex has one of the following general structures I:

Ia

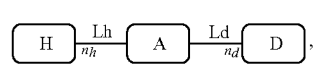

,

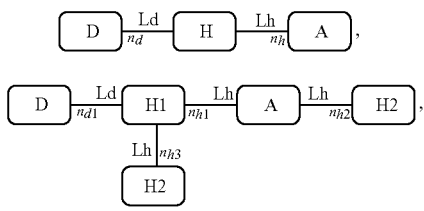

wherein A is nanocarrier, such as a polysaccharide or polypeptide; H, H1 and H2 are one or more different helper moieties; D is one or more autoimmune disease-specific antigens; Ld and Lh are one or more different links or linkers in covalent or non-covalent binding; $n_h$, $n_{h1}$ and $n_{h2}$ are the number of helper groups attacked to A; $n_{h3}$ is the number of helper groups attacked to other helper groups; $n_{d2}$ is the number of antigens groups attacked to A; and $n_{d1}$ is the number of antigen groups attacked to a helper group.

When the carrier A is selected from one of the polysaccharides known for such purposes, such as chitosan or pullulan, it is not necessary to include carbohydrates as helper moiety. In order to create a nanoparticle of the right size for not penetrating cell membranes and for securing solubility in the blood stream, helper moieties such as hyaluronic acid may be conjugated to a chitosan core. The chitosan and/or the helper moiety, e.g. hyaluronic acid, may be further decorated with surface neutralizing helper moieties, such as for example PEG. Chitosan, hyaluronic acid and PEG are all known not to be toxic or immunogenic, and thus relatively safe for use in medical treatment. The antigen can be attached to the carries, e.g. chitosan, or one of the helper moieties, e.g. hyaluronic acid or PEG. All moieties may be conjugated by covalent or non-covalent binding.

1.2 Specific Antigen Component of the Nanoconjugate Complex

The autoimmune disease specificities of the nanoconjugate complexes are limited to the conjugated antigens. All helper moiety selected from carbohydrates, lipids, polymers as well as the carries are not disease specific, but contribute to the complex by adding further beneficial properties as described. The patterns in individual patients vary; in other words the same antigens get recognized but at a different level across antigens for each patient. Selection of disease specific antigen sequences may be done by traditional antigen library screening, or more time and cost efficient by rational design, using a combination of computational and laboratory screening, supported by studying available literature. A successful disease specific antigen is stable, with a high affinity for the disease associated autoantibody in the patient.

The specific antigen of the nanoconjugate complex of the present invention, recognized by autoantibodies related to an autoimmune disease, may be a nucleic acid sequence, a peptide, a phospholipid or other cell-related components. The nanoconjugate complex comprises at least one specific antigen, i.e. one or more specific antigen(s). If the specific antigen is present in more than one copy, all copies may be the same or different. If the specific antigens are a combination of different antigens within the same nanoconjugate complex, such a combination may be of different oligonucleotides within the same nanoconjugate complex, different peptides within the same nanoconjugate complex, or a mixture of oligonucleotide(s) and a peptide(s) within the same nanoconjugate complex.

In one embodiment, the specific antigen(s) is/are the same or difference and selected from peptide(s) and oligonucleotide(s) related to autoimmune kidney disease. In another embodiment, the specific antigen(s) is/are the same or difference and selected from peptide(s) and oligonucleotide(s) related to RA.

Peptides related to autoimmune kidney disease may be selected from peptides mimicking histone H3 peptides owing to confirmed efficacy of ANA binding, such as SEQ ID NO. 3. Further, for reducing potential toxicity and cost of a therapeutic, a part of the original sequence may be used, such as SEQ ID NO. 5 and SEQ ID NO. 6, which are derived from SEQ ID NO. 3. Further, clearance of autoantibodies-nanoconjugate complexes may be improved by liver targeting peptides, such as SEQ ID NO. 4.

Oligonucleotides related to autoimmune kidney disease may be selected from DNA sequences target by anti-DNA antibodies in SLE disease. SEQ ID NO. 1 and SEQ ID NO. 2 are examples of such oligonucleotides. Other examples are SEQ ID NO. 7 and SEQ ID NO. 8, where SEQ ID NO. 8 is anti-SLE specific.

In a further embodiment, the autoimmune kidney disease specific antigen is characterized by being recognized by autoantibodies related to autoimmune kidney disease and is selected from oligonucleotides SEQ ID NO. 1, SEQ ID NO. 2 and SEQ ID NO. 8 as well as oligonucleotides with >60% sequence identity to SEQ ID NO. 1, SEQ ID NO. 2 or SEQ ID NO. 8; in another embodiment, the autoimmune kidney disease specific antigen is selected from peptides SEQ ID NO. 3, SEQ ID NO. 4, SEQ ID NO. 5, and SEQ ID NO. 6 as well as peptides with >60% sequence identity to SEQ ID NO. 3, SEQ ID NO. 4, SEQ ID NO. 5, or SEQ ID NO. 6; in yet another embodiment, the autoimmune kidney disease specific antigen is a combination of two of more of SEQ ID NO. 1, SEQ ID NO. 2, SEQ ID NO. 3, SEQ ID NO. 4, SEQ ID NO. 5, SEQ ID NO. 6 and SEQ ID NO. 8 as well as sequences with >60% sequence identity to any of the selected SEQ ID NO. 1, SEQ ID NO. 2, SEQ ID NO. 3, SEQ ID NO. 4, SEQ ID NO. 5, SEQ ID NO. 6 and SEQ ID NO. 8.

In a further embodiment, the autoimmune kidney disease specific antigen is characterized by being recognized by autoantibodies related to autoimmune kidney disease and is selected from oligonucleotides SEQ ID NO. 1, SEQ ID NO. 2 and SEQ ID NO. 8 as well as oligonucleotides with >80% sequence identity to SEQ ID NO. 1, SEQ ID NO. 2 or SEQ ID NO. 8; in another embodiment, the autoimmune kidney disease specific antigen is selected from peptides SEQ ID NO. 3, SEQ ID NO. 4, SEQ ID NO. 5, and SEQ ID NO. 6 as well as peptides with >80% sequence identity to SEQ ID NO. 3, SEQ ID NO. 4, SEQ ID NO. 5, or SEQ ID NO. 6; in yet another embodiment, the autoimmune kidney disease specific antigen is a combination of two of more of SEQ ID NO. 1, SEQ ID NO. 2, SEQ ID NO. 3, SEQ ID NO. 4, SEQ ID NO. 5, SEQ ID NO. 6 and SEQ ID NO. 8 as well as sequences with >80% sequence identity to any of the selected SEQ ID NO. 1, SEQ ID NO. 2, SEQ ID NO. 3, SEQ ID NO. 4, SEQ ID NO. 5, SEQ ID NO. 6 and SEQ ID NO. 8.

In a further embodiment, the autoimmune kidney disease specific antigen is characterized by being recognized by autoantibodies related to autoimmune kidney disease and is selected from oligonucleotides SEQ ID NO. 1, SEQ ID NO. 2 and SEQ ID NO. 8 as well as oligonucleotides with greater than 82, 84, 86, 88, 90, 92, 94, 96, or 98% sequence identity to SEQ ID NO. 1, SEQ ID NO. 2 or SEQ ID NO. 8; in yet another embodiment, the autoimmune kidney disease specific antigen is selected from peptides SEQ ID NO. 3, SEQ ID NO. 4, SEQ ID NO. 5, and SEQ ID NO. 6 as well as peptides with greater than 82, 84, 86, 88, 90, 92, 94, 96, or 98% sequence identity to SEQ ID NO. 3, SEQ ID NO. 4, SEQ ID NO. 5, or SEQ ID NO. 6; in another embodiment, the autoimmune kidney disease specific antigen is a combination of two of more of SEQ ID NO. 1, SEQ ID NO. 2, SEQ ID NO. 3, SEQ ID NO. 4, SEQ ID NO. 5, SEQ ID NO. 6 and SEQ ID NO. 8 as well as sequences with greater than 82, 84, 86, 88, 90, 92, 94, 96, or 98% sequence identity to any of the selected SEQ ID NO. 1, SEQ ID NO. 2, SEQ ID NO. 3, SEQ ID NO. 4, SEQ ID NO. 5, SEQ ID NO. 6 and SEQ ID NO. 8.

In a preferred embodiment, the autoimmune kidney disease specific antigen of the nanoconjugate complex is oligonucleotide SEQ ID NO. 1 or any oligonucleotides with >80% sequence identity to SEQ ID NO. 1. In a more preferred embodiment, the autoimmune kidney disease specific antigen of the nanoconjugate complex is oligonucleotide SEQ ID NO. 1.

In a preferred embodiment, the autoimmune kidney disease specific antigen of the nanoconjugate complex is oligonucleotide SEQ ID NO. 1 or any oligonucleotides with greater than 80, 82, 84, 86, 88, 90, 92, 94, 96, or 98% sequence identity to SEQ ID NO. 1. In a more preferred embodiment, the autoimmune kidney disease specific antigen of the nanoconjugate complex is oligonucleotide SEQ ID NO. 1.

Differences within the antigen sequences between different patients are one reason for differences in sequence identity as discussed above. Another reason is the possibility of changes in the antigen leading to the same or enhanced recognition and/or binding to the autoantibodies.

RA and certain forms of psoriasis are known to be related to the presence of citrullinated proteins or peptide in affected patients. Specific citrullinated peptide epitopes can be selected by screening of protein fragments and their mutated variants in for example RA sera. As an example, a library of 25 citrullinated peptide epitopes derived from fibrinogen, vimentin and histone 3 were screened against sera from RA patients and one of these peptides were found to bind RA sera selectively. Having selected the most potent peptide epitope, it was included into nanoparticles loaded for evaluation by a series of in vitro assays. The library screened comprised the citrullinated peptides SEQ ID NO. 9 to SEQ ID NO. 33. SEQ ID NO. 10 has been shown to comprise a RA-autoantibody-specific antigen epitope.

In a preferred embodiment, the autoimmune RA specific antigen of the nanoconjugate complex is peptide SEQ ID NO. 10 or any peptide with >80% sequence identity to SEQ ID NO. 10. In a more preferred embodiment, the autoimmune RA specific antigen of the nanoconjugate complex is peptide SEQ ID NO. 10 or any oligonucleotides with greater than 80, 82, 84, 86, 88, 90, 92, 94, 96, or 98% sequence identity to SEQ ID NO. 10. In a most preferred embodiment, the autoimmune RA specific antigen of the nanoconjugate complex is peptide SEQ ID NO. 10.

1.3 Lipid Component of a Nanoconjugate Complex with Structure II

Lipids influence the transport, biodistribution, efficacy and cellular uptake of different drugs; hence lipids can facilitate increased solubility and adsorption as well as enhanced bioavailability. The lipid component of the nanoconjugate complex acts as a clearance signal for the antibody:nanoconjugate complex [Hutchinson et al, Pept Sci. 2017 February; 23(2):82-94]. This is not limited to a certain fatty acid, however longer chains (C7 and greater) are known to target the molecules to the liver and enhance digestion. Moreover, together with PEG (see below), the lipid component improves biodistribution and prolongs half-life in serum.

The nanoconjugate complex comprises at least one lipid, i.e. one or more lipid(s). If the lipid is present in more than one copy, all copies may be the same or different.

In one embodiment, the lipid component of the nanoconjugate complex is one or more fatty acid(s), selected from the natural aliphatic fatty acids such as those readily available from commercial suppliers.

The fatty acids may be straight chain or branched; they may be saturated, unsaturated or a combination hereof. In a preferred embodiment, the fatty acids of the nanoconjugate complex of the present invention are unbranched and saturated. In a preferred embodiment the lipid component of the nanoconjugate complex is selected from enanthic (heptanoic) acid, caprylic acid, pelargonic acid, capric acid, undecylic acid, lauric acid, tridecylic acid, myristic acid, pentadecylic acid and palmitic acid.

In another embodiment, the lipid component may be a combination of different lipids within the same nanoconjugate complex, such as a combination of two or more different fatty acids within the same nanoconjugate complex, such as where the fatty acids are selected from caproic (hexanoic) acid, enanthic (heptanoic) acid, caprylic acid, pelargonic acid, capric acid, undecylic acid, lauric acid, tridecylic acid, myristic acid, pentadecylic acid and palmitic acid.

1.4 Carbohydrate Component of a Nanoconjugate Complex with Structure II

The carbohydrate component of the nanoconjugate complex increases the solubility of the lipidated molecule. Simultaneously a carbohydrate might promote clearance of the inflammation-causing dead cells and their parts (called microparticles) as well as apoptotic bodies. Recently, it has been shown that microparticles are being extensively secreted to the blood of patients having autoantibody-related kidney disease [Giannella et al. Cardiovasc Diabetol. 2017; 16: 118]. These particles contain surface proteins that recognize specific carbohydrates. A carbohydrate component is therefore included in the nanoconjugate complex of the present invention to help clear these.

The nanoconjugate complex comprises at least one carbohydrate, i.e. one or more carbohydrate(s). If the carbohydrate is present in more than one copy, all copies may be the same or different.

In one embodiment the carbohydrate component of the nanoconjugate complex is selected from the available literature on microparticle surface glycosylation. Glucosamine is a prominent precursor in the biochemical synthesis of glycosylated proteins and lipids. Other carbohydrates related to microparticle surface glycosylation comprise D-mannose, D-galactose and their oligomers. Diverse carbohydrates can be applied depending on the overall conjugate design. The carbohydrates may be a mono-, di-, poly-, or oligosaccharide.

In one embodiment the carbohydrate component of the nanoconjugate complex is selected from mannose, galactose, glucosamine, and their oligomers. In a preferred embodiment the carbohydrate component of the nanoconjugate complex is selected from galactose and glucosamine.

In a further embodiment, the carbohydrate component may be a combination of different carbohydrates within the same nanoconjugate complex, such as a combination of two or more different carbohydrates selected from mannose, galactose, glucosamine, and their oligomers.

1.5 Polymer Component of a Nanoconjugate Complex with Structure II

The nanoconjugate complex comprises a polymer component to ensure the stability in biofluids and antigen representation to the autoantibody (IgG, IgA or IgM). A polymer such as PEG can, by increasing the molecular weight of a molecule, impart several significant pharmacological advantages, such as improved drug solubility, extended circulating life, increased drug stability, and enhanced protection from proteolytic degradation. Therefore the polymer needs to be hydrophilic. With regard to the size, the polymer can be a broad range, such as starting with PEG3000 and going up to PEG20000. PEGylation thereby aids in the effective delivery of the nanoconjugate complex to the targeted destination. Human serum albumin (HSA) is another option to achieve these beneficial properties.

The nanoconjugate complex comprises at least one polymer, i.e. one or more polymer(s). If the polymer is present in more than one copy, all copies may be the same or different.

In one embodiment, the polymer component of the nanoconjugate complex may be selected from functionalized carbohydrates such as chitosan and pullulan, or protein derivatives that are known to improve biodistribution of biological drugs such as human serum albumin. In a preferred embodiment, the polymer of the nanoconjugate complex is PEG. PEG is commercially available in different forms and can be selected in combination with the carrier and other helper moiety properties of the nanoconjugate complex.

In another embodiment, the polymer component may be a combination of different polymers within the same nanoconjugate complex, such as a combination of two or more polymers selected from PEG, chitosan, pullulan and human serum albumin.

1.6 Links or Linkers of the Nanoconjugate Complex

The links or linkers Lb, Lc, Ld, Le, in Structure II connect the antigen, carbohydrate, lipid and polymer components to the backbone and Ld and Lh in structure I connect the antigen and helper moiety to the backbone. The selection of conjugation chemistry depends on the chemical properties of the starting material and the desired stability of the bond created in the product. The links or linkers may be the same or different. In a preferred embodiment, the linkers may be any functional group such as ether, ester, disulfide, amide, 1,2,3-triazole, or PEG. Alternatively, the link may be non-covalent, such as an electrostatic interaction.

In a further embodiment, the linkers may comprise a combination of two or more functional groups within one linker, the functional groups being selected from ether, ester, disulfide, amide, 1,2,3-triazole, and PEG.

In a selected embodiment, the link is non-covalent.

2 Preparation of Nanoconjugate Complexes

A second aspect of the invention relates to a method for preparing nanoconjugate complexes of the present invention.

In one embodiment, the nanoconjugate complex of structure I of the present invention is prepared by a method comprising the steps:

a. providing a nanocarrier for use in connecting all the components of the nanoconjugate complex
b. linking at least one helper moiety to the carrier
c. linking at least one specific antigen to the carrier or the helper moiety wherein step b and c may be carried out in any order or be combined.

In another embodiment, the nanoconjugate complex of structure II of the present invention is prepared by a method comprising the steps:

a. providing a nanocarrier for use in connecting all the components of the nanoconjugate complex as set forth in steps b-e,
b. linking at least one polymer component to the carrier
c. linking at least one specific antigen component to the carrier
d. linking at least one lipid component to the carrier
e. linking at least one carbohydrate component to the carrier wherein two or more of the steps b, c, d, and e may be combined; and the steps may be carried out in any chosen order In any embodiment of preparing nanoconjugates, covalent binding or non-covalent binding may be chosen as desired. For covalent binding, click chemistry is the preferred synthesis and well known in the art. Additional dialysis and labelling steps may further be introduced where needed, as identified by a person skilled in the art.

With regard to the structure of the assembly, the different components may be linked randomly to the carrier backbone, or the location may be preselected. Further, multiple units of each component may be linked to the backbone of the nanoconjugate complex, such that the final nanoconjugate complex comprises one or more of each component. There is no defined restriction on the ratio of the components. The available functional surface groups on the carrier define to upper limit of the total number of the components. Preferably between 10 and 70% of the available surface groups are occupied by the antigen(s) and the helper moieties. More preferred, between 20 and 50% of the groups are occupied.

The antigen and helper moieties, such as carbohydrate, lipid, and polymer components, may be linked to the backbone of the nanoconjugate complex by covalent attachment, such as through linkers or links as specified below; or may be linked by noncovalent attachment. In a preferred embodiment, the linkers may be any functional group such as ether, ester, disulfide, amide, 1,2,3-triazole, or PEG. Alternatively, the link may be noncovalent such as an electrostatic interaction. In further embodiment, the linkers may comprise a combination of two or more functional groups within one linker, the functional groups being selected from ether, ester, disulfide, amide, 1,2,3-triazole, and PEG. Depending on the type of link or linker, different attachment protocols known by a person skilled within the art may be used to connect the different components of the nanoconjugate complex, such as including but not limited to standard PEGylation, click chemistry attachment, and NHS (N-hydroxysuccinimide) chemistry attachment protocols.

In one embodiment, the nanoconjugate complex is PEGylated. PEGylation is the process of attaching strands of the polymer PEG to molecules, thereby producing alterations in the physiochemical properties including changes in conformation, electrostatic binding, hydrophobicity etc. PEGylation may be performed according to standard protocols known by a person skilled in the art, such as done by hydroxysuccinimide chemistry [Alibolandi et al. 2017. Int J Pharm 519, 352-364].

In one embodiment, one or more selected component(s) of the nanoconjugate complex is linked to the backbone by noncovalent attachment by slowly adding the component(s) in a preselected ratio to a stirred solution containing the backbone and let the mixture incubate for a sufficient time period.

In another embodiment, one or more selected component(s) of the nanoconjugate complex is linked to the backbone by click chemistry [WO2007011967A2]. The reaction may be performed according to standard protocols known by a person skilled in the art, such as done by the classic copper-catalyzed click reaction of an azide and an alkyne [Development and Applications of Click Chemistry. Gregory C. Patton. Nov. 8, 2004]. In a preferred embodiment, the pH may vary from acidic to basic, but concentrations of the reaction components shall be kept in a low milimolar range.

In another embodiment, a selected component of the nanoconjugate complex is linked to the backbone by NHS (N-HydroxySuccinimide) ester reaction with free amino groups. Amino groups are nearly always contained in proteins and peptides, modification of these biopolymers by NHS ester reaction is therefore especially common. Other examples are amino-oligonucleotides, amino-modified DNA, and amino-containing sugars. The reaction may be performed according to standard protocols known by a person skilled in the art. The reaction of NHS esters with amines is strongly pH-dependent: at low pH, the amino group is protonated, and no modification takes place. At higher-than-optimal pH, hydrolysis of NHS ester is quick, and modification yield diminishes. In a preferred embodiment, pH value for NHS (N-hydroxysuccinimide) ester reaction is 8.3-8.5.

Compared to the standard multi-step synthesis of low molecule therapeutic drugs, the preparation of the nanoconjugate complex of the present invention is experimentally simple as is evident from the above description as well as example 1. The synthesis scheme is flexible and can be adjusted for the specific nanoconjugate composition, aiming at the most efficient representation of the antigen within the product.

3. Treating Autoimmune Diseases with Nanoconjugate Complexes

A third aspect of the invention relates to a pharmaceutical composition comprising the nanoconjugate complex. The therapeutic nanoconjugate complex may be of the general structure I or II, or may comprise a combination of two or more nanoconjugate complexes, such as complexes comprising different specific antigens, different carbohydrates, different lipids, or even different polymers. For example, the pharmaceutical combination comprises two different complexes, wherein the antigen is different, such as two different oligonucleotides, two different peptides or a combination of oligonucleotide(s) and peptide(s). In the same way the pharmaceutical combination may comprise three or even more different nanoconjugate complexes.

The nanoconjugate complex may be part of a pharmaceutical composition further comprising existing low molecular drugs and biologics (for example methotrexate and/or a monoclonal antibody such as Rituximab [Cravedi. G Ital Nefrol. 2012 May-June; 29(3):274-82; discussion 292]).

Important requirements for therapeutic drugs include low toxicity, high target binding specificity, and prolonged effect in vivo. These properties are obtained in the nanoconjugate complex of the present invention by combining multiple active components within one complex: active antigen, solubilizing reagents, several state-of-the-art helper molecules that aid sufficient biodistribution and clearance from the blood stream when the target antibody is recognized and bound. Further, most of the components of the nanoconjugate complex of the present inventions are biomolecules; this ensures low toxicity of the therapeutic product.

A fourth aspect of the invention relates to using the nanoconjugate complex in treating autoimmune diseases, such as autoimmune kidney disease, RA, psoriasis, T1D, sclerosis and others, and provides a method of treatment comprising the steps:
a. providing at least one nanoconjugate complex or a pharmaceutical composition according to the invention; and
b. administering said nanoconjugate complex(es) or said pharmaceutical composition to a patient suffering from an autoimmune disease.

Patients to be treated with the nanoconjugate complex may be humans or animals suffering from CKD, caused by autoantibodies, RA or other autoimmune diseases at any disease stage.

The nanoconjugate complex may be administered to the patient by intravenous injection, transfusion, intramuscular injection, or by other such methods known by a person skilled in the art for administering pharmaceutical complexes. The nanoconjugate complex may be administered in several dosages with a selected interval for a selected period of time. The use of therapeutic may be adjusted based on measurements of autoantibody levels in the blood. It is most preferred to administer the nanoconjugates directly to the blood stream by iv administration.

The therapeutic nanoconjugate complex of the present invention addresses the cause of kidney disease, RA and other auto immune diseases and is in that way safer and more efficient than currently used symptomatic drugs. Using this nanomaterial, the autoimmune diseases can be treated earlier in its course and with a better outcome for the patient since the tissue damage by chronic inflammation is prevented.

EXAMPLES

The following examples are merely intended to illustrate the principle of the present invention and therefore in no way intended to limit the scope of the claimed invention.

Example 1: In Vitro Assay—Identification of Suitable SLE/CKD Antigens

The suitability of different possible antigens aiming at autoantibodies involved in kidney autoimmune disease (Table 1) was tested prior to synthesizing nanoconjugate complexes. Oligonucleotides relating to autoimmune kidney disease were selected from DNA sequences targeted by anti-DNA antibodies in SLE disease. TCCTTTCTTTCTTTCTT (SEQ ID NO. 1) and (TTAGGGTTAGGGTTAGGGTTAGGGTTAG) SEQ ID NO. 2 were selected for testing such oligonucleotides. One tested peptide, ARTKQTARKSTGGKAPGGC (SEQ ID NO. 3) relates to autoimmune kidney disease mimicking histone H3 peptides owing to a confirmed efficacy of ANA binding. Parts of the original sequence, ARTKQTAR (SEQ ID NO. 5) and KQTARKSTGGKAP (SEQ ID NO. 6), derived from SEQ ID NO. 3 are also tested.

TABLE 1

Selected antigens aiming at kidney disease.

| Component | Antigen Sequence |
|---|---|
| D1 | Oligonucleotide:<br>5' TCCTTTCTTTCTTTCTT 3' (SEQ ID NO. 1) |

TABLE 1-continued

Selected antigens aiming at kidney disease.

| Component | Antigen Sequence |
|---|---|
| D2 | G-quadruplex oligonucleotide:<br>5' TTAGGGTTAGGGTTAGGGTTAGGGTTAG 3'<br>(SEQ ID NO. 2) |
| D3 | Histone peptide:<br>ARTKQTARKSTGGKAPGGC (SEQ ID NO. 3) |
| D4 | P41 peptide:<br>SWLRRIWRWICKVLSRFK (SEQ ID NO. 4) |
| D5 | Histone peptide H3s1:<br>Ac-ARTKQTAR (SEQ ID NO. 5) |
| D6 | Histone peptide H3s2:<br>Ac-KQTARKSTGGKAPG (SEQ ID NO. 6) |

SEQ ID NO. 4 is a liver targeting peptide which when attached to the carries may be used to improve the clearance of the autoantibodies-nanoconjugate complexes.

Binding of antigens shown in Tables 1 to SLE/CKD disease stated sera was confirmed by enzyme linked immunosorbent assay (ELISA). Maxisorb 96 well plates (NUNC Thermofisher, Germany) were coated with individual antigens at concentration 5 μg/mL in 1×PBS overnight (room temperature; 150 μl/well). After washing with 1×PT (2×300 μl/well, PT: 50 μl Tween-20 in 1 L 1×PBS), the plates were blocked with 1×PTB (1 h, 37° C.; 100 μl/well, PTB: 20 g BSA, 50 μl Tween-20 in 1 L 1×PBS). Incubation with SLE/CKD plasma at desired dilution was performed at 37° C. for 1.5 h using diluent: 2 g BSA, 50 μl Tween-20 in 1 L 1×PBS (100 μl/well). This was followed by washing (2×300 μl 1×PBS) and incubation with HPR-labelled secondary antibody for 1.5 h at 37° C. using same diluent and dilution of the secondary antibody provided by supplier (HPR-conjugated a-aIgG or a-aIgM; Sigma). Subsequent washing (2×300 μl PT) and incubation with freshly prepared TMB-H$_2$O$_2$ solution (Sigma; 100 μl/well) was followed by adding a stop solution (1M H2SO4; 50 μl/well) and reading resulting absorbance values at 450 nm on Magellan Tecan microplate reader.

Linear range for each antigen (D1, D2, D3 and D4) was determined via testing series of control dilutions (control sera purchased from Immunovision in dilutions 1:50 to 1:2000). The linearity confirmed that the selected concentration range was suitable for the detection of antibodies, and that other sera/assay components did not interfere with the result. According to the results plasma dilutions 1:100-1:500 were within linear range of the assay for each antigen ($R^2$>0.95).

Example 2: Synthesis of Nanoconjugate Complexes

Different nanoconjugate complexes aiming at kidney autoimmune disease were prepared as described below.

2.1 Composition of the Synthesized Nanoconjugate Complexes

The synthesized nanoconjugates complexes comply with the general Structure II:

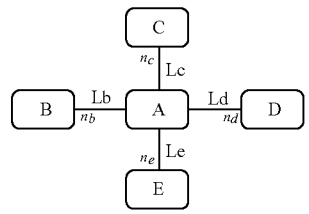

II wherein A is a nanoparticle backbone/carrier to which at least one ($n_b$) lipid (B), at least one ($n_c$) carbohydrate (C), at least one kidney autoimmune disease specific antigen ($n_d$) (D), and at least one ($n_e$) polymer (E) are attached through links or linkers Lb, Lc, Ld, and Le, respectively.

The compositions of each of the synthesized nanoconjugate complexes are summarized in Table 2 with the different components further specified in Table 3.

TABLE 2

Composition of synthesized nanoconjugate complexes for treatment of kidney disease (No. 1-5, and 7-8) and controls (No. 6, 9 and 10)

| Conjugate no. | Composition |
|---|---|
| 1 | A + B1 + C1 + D1 + E |
| 2 | A + B2 + C1 + D1 + E |
| 3 | A + B2 + C2 + D1 + E |
| 4 | A + B1 + C1 + D4 + E |
| 5 | A + B1 + C2 + D4 + E |
| 6 | A + C1 + D1 + E |
| 7 | A + B1 + C1 + D5 + E |
| 8 | A + B1 + C1 + D6 + E |
| 9 | A + C1 + D5 + E |
| 10 | A + C1 + D6 + E |

TABLE 3

Specification of the components of the nanoconjugate complexes
Components

| A | PAMAM polymer (G5) |
|---|---|
| B1 | Heptanoic acid |
| B2 | Pentadecanoic acid |
| C1 | Galactose |
| C2 | Glucosamine |
| D1 | Oligonucleotide:<br>5' TCCTTTCTTTCTTTCTT 3' (SEQ ID NO. 1) |
| D2 | G-quadruplex oligonucleotide:<br>5' TTAGGGTTAGGGTTAGGGTTAGGGTTAG 3'<br>(SEQ ID NO. 2) |
| D3 | Histone peptide:<br>ARTKQTARKSTGGKAPGGC (SEQ ID NO. 3) |
| D4 | P41 peptide:<br>SWLRRIWRWICKVLSRFK (SEQ ID NO. 4) |
| D5 | Histone peptide H3s1:<br>(acetylated)-ARTKQTAR (SEQ ID NO. 5) |
| D6 | Histone peptide H3s2:<br>(acetylated)-KQTARKSTGGKAPG (SEQ ID NO. 6) |
| E | PEG3000 |

Figure 2:
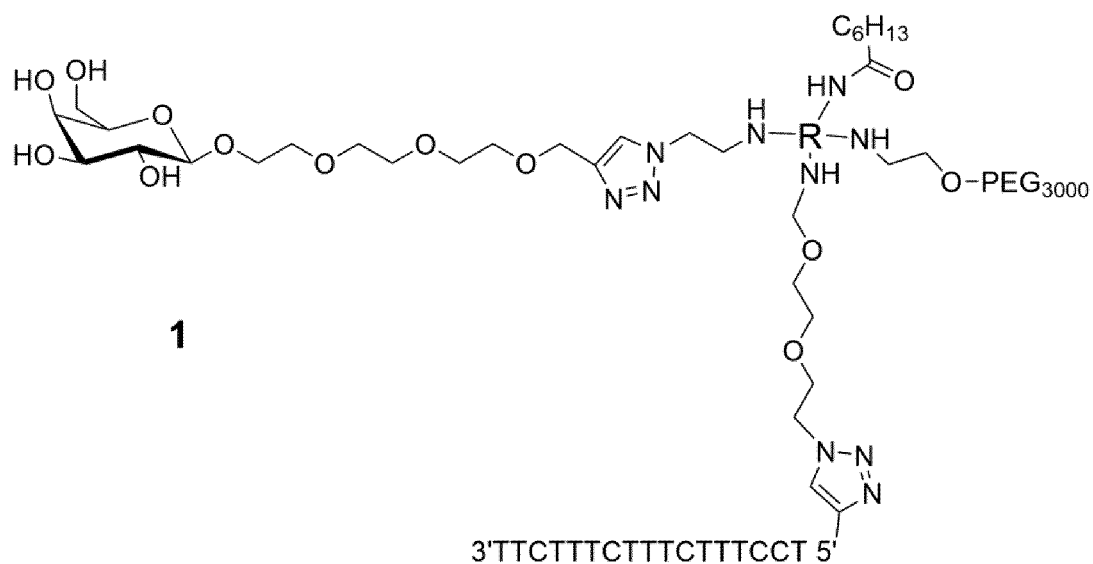
FIG. 2. Illustration of synthesized nanoconjugate complexes 1-10. R=PAMAM G5 is the carrier and backbone for all the synthesized nanoconjugate complexes. This backbone provides 128 surface groups that represents available attachment sites for the carbohydrate, lipid, polymer, and antigen components. Hence, each of the four components may theoretically be present in 1 to 125 copies, while the sum of all the components may not exceed 128.
Figure 2:
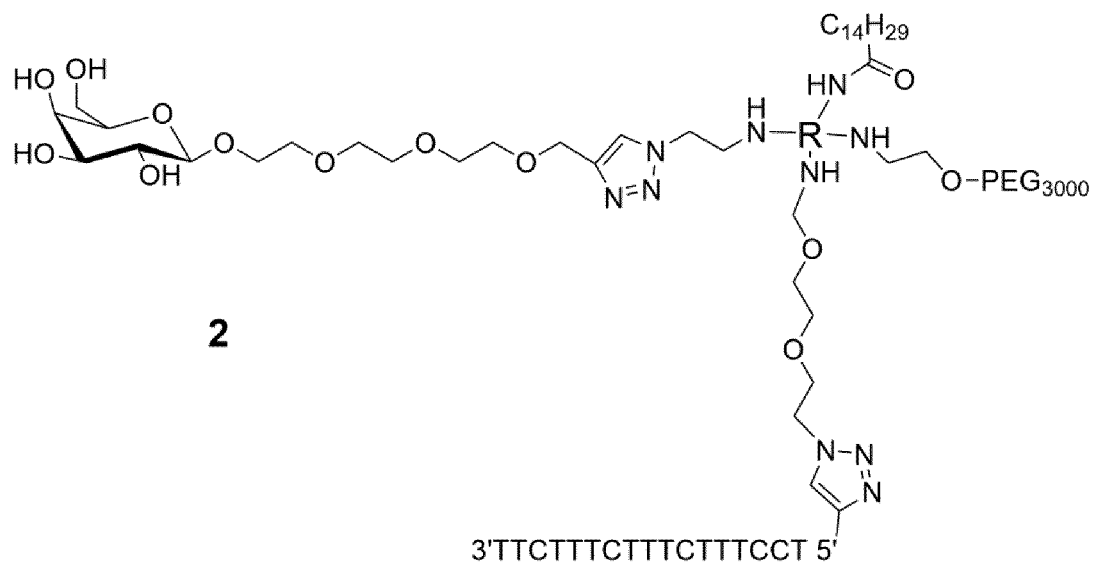
Figure 2:
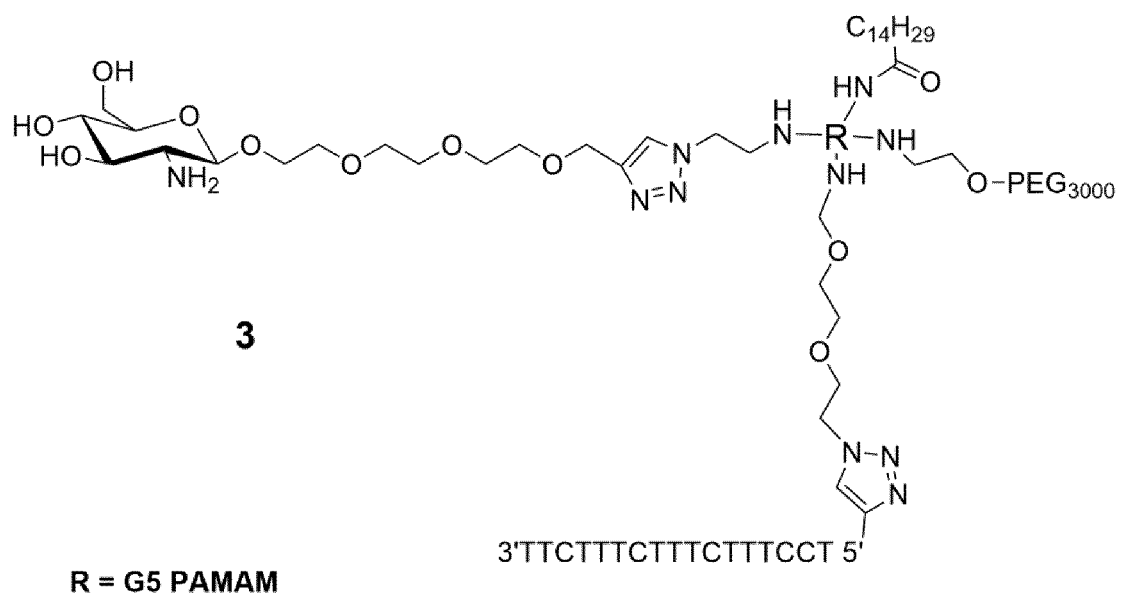
Figure 2:
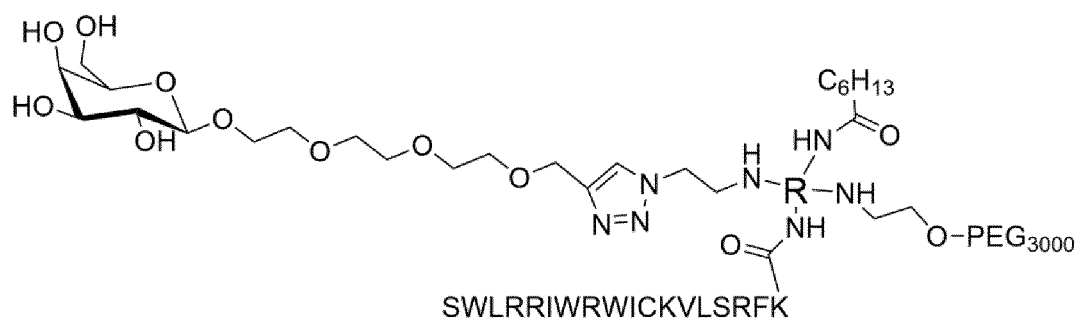
Figure 2:
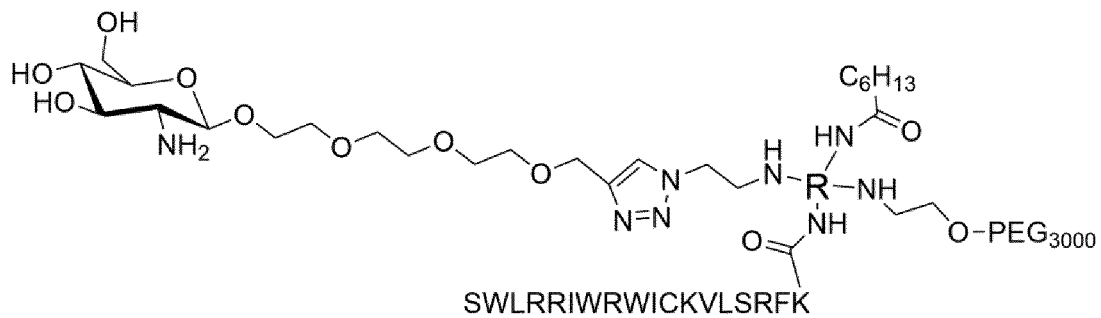
Figure 2:
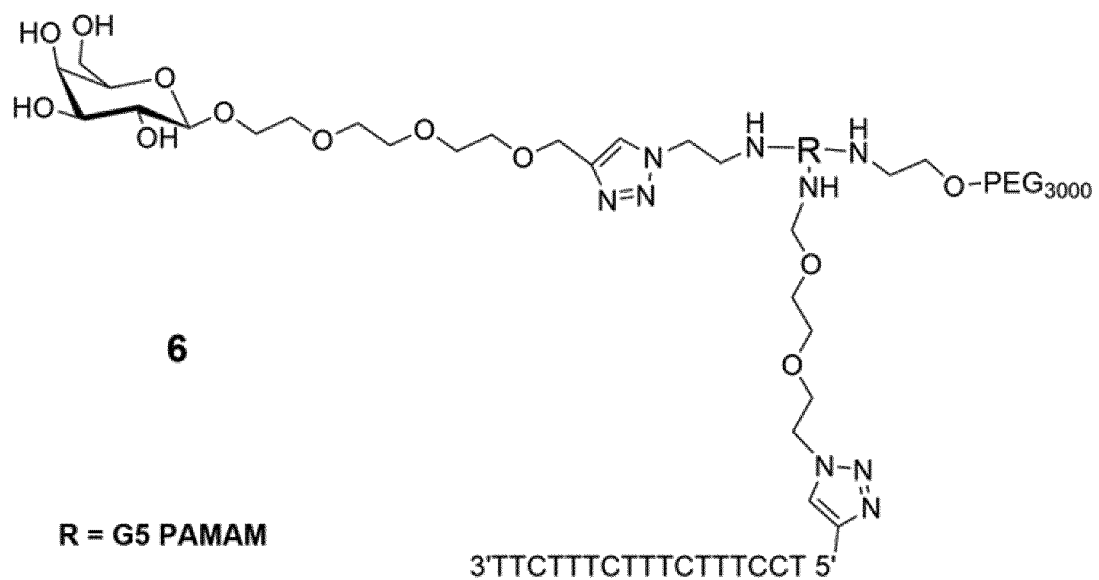
Figure 2:
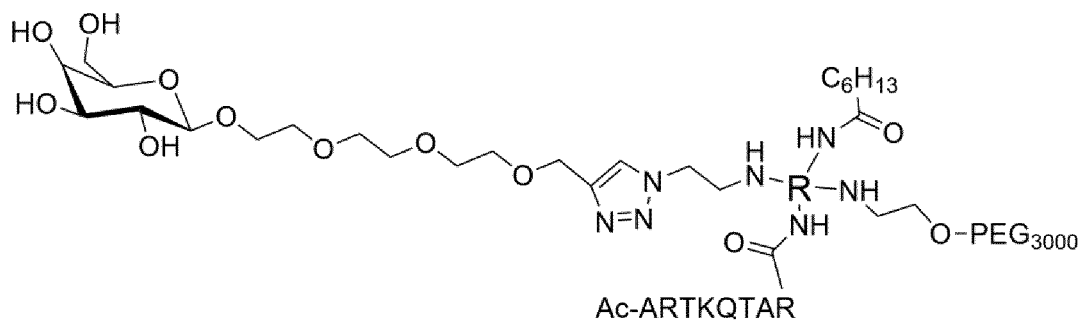
Figure 2:
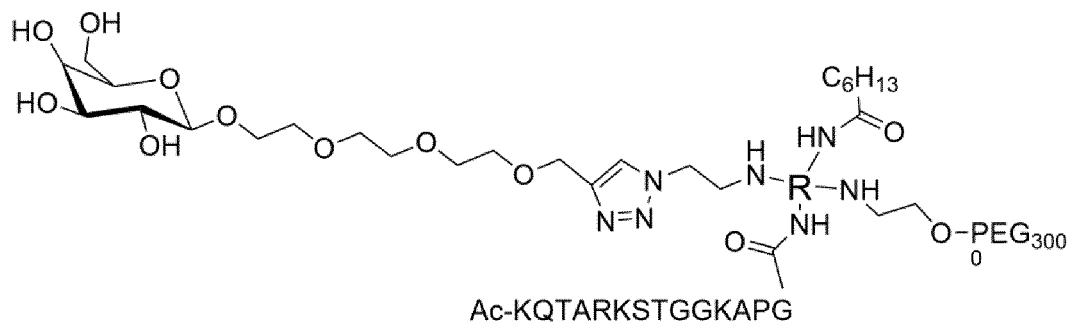
Figure 2:
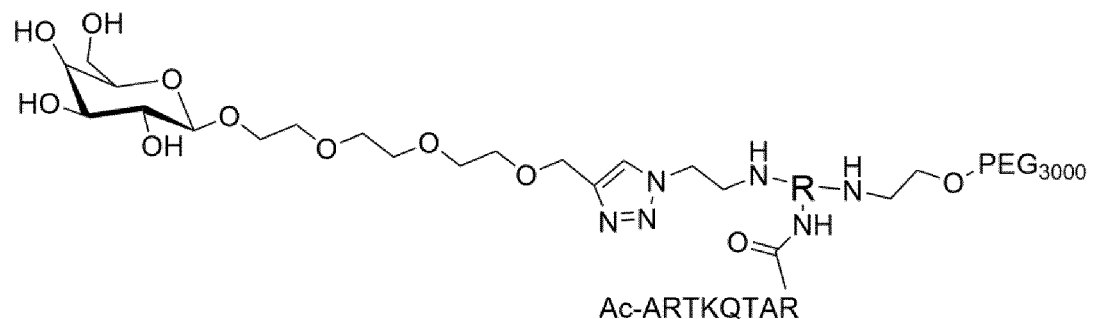
Figure 2:
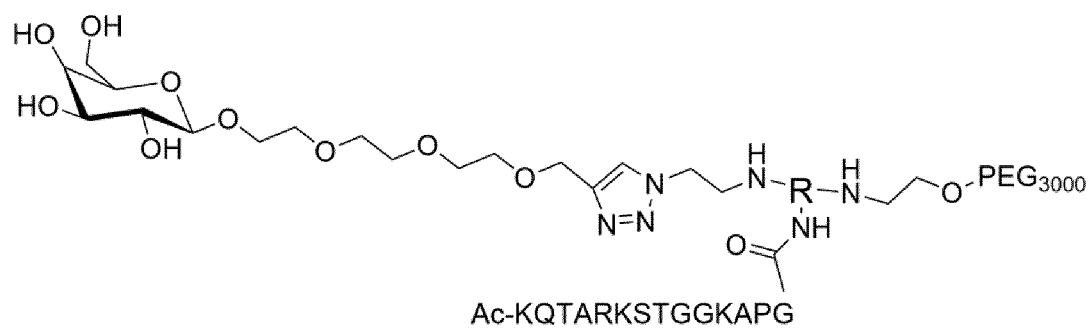

In FIG. 2, the synthesized nanoconjugate complexes 1-10 are illustrated. PAMAM G5 is the backbone carrier (A) for the synthesized nanoconjugate complexes. This backbone carrier provides theoretically 128 surface amino groups that represents available attachment sites for the lipid (B), carbohydrate (C), antigen (D) and polymer (E) components. Hence, each of the four components (B, C, D, and E) may theoretically be present in 1 to 125 copies, while the sum of all the components cannot exceed 128. The ratio between the different components is not fixed, though a ratio of B:C:D:E of 1:3:1:2 was intended by the synthesis protocol described below. Further, in the case of the synthesized nanoconjugate complexes (No. 1-5, and 7-8) and controls (No. 6, 9 and 10), only a total of approximately 25-30% of the surface groups of the backbone carrier were occupied by components B, C, D, and E.

2.2 Reagent, Material, Etc. For Synthesis of the Nanoconjugate Complexes

All the reagents and buffers used in the preparation of the nanoconjugate complexes are listed in Table 4. Reagents and buffers obtained from commercial suppliers were used as received.

TABLE 4

Used reagents and buffers

| Reagent/buffer | Origin |
|---|---|
| D-(+)-Galactose | G0750 Sigma-Aldrich Denmark |
| D-Glucosamine | CDS021691 Aldrich Denmark |
| PAMAM Ethylenediamine core, generation 5.0 | 536709 Aldrich USA |
| Heptanoic acid | 75190 Sigma Denmark |
| Pentadecanoic acid | W433400 Sigma Denmark |
| DNA Oligonucleotide: 5' TCCTTTCTTTCTTTCTT 3' | custom ordered from IDT, Belgium |
| G-quadruplex forming DNA oligonucleotide: 5' TTAGGGTTAGGGTTAGGGTTAGGGTTAG 3' | custom ordered from IDT, Belgium |
| Peptide: ARTKQTARKSTGGKAPGGC | custom ordered from Caslo lab, Denmark |
| Peptide: SWLRRIWRWICKVLSRFK | custom ordered from Caslo lab, Denmark |
| Peptide: (acetylated) ARTKQTAR | Made in-house at DTU Chemistry, Denmark |
| Peptide: (acetylated) KQTARKSTGGKAPG | Made in-house at DTU Chemistry, Denmark |
| PEG3000 | Sigma Aldrich Denmark 81230 |
| PBS buffer tablets | Sigma Denmark P4417 |
| MQ water: prepared by deionizer (Milipore) in house | (DTU Chemistry, Denmark) |
| Sodium bicarbonate | Sigma Denmark S5761 |
| 10K Dialysis kit | Thermo fisher Germany 88404 |

The following plastics and other minor equipment was used:

Microcentrifuge tubes (Thermo Germany, 2150N), glass vials (VWR Denmark, 113459), pipetman set (Gilson, Inc, UK, PIPETMAN® Classic), pipet tips (Gilson, Inc, UK, PIPETMAN DIAMOND Tips—Sterilized Filter Tips, 14324), shaker (Eppendorf Innova® S44i Shaker, USA), centrifuge (Thermo fisher Germany, R0165).

2.3 Synthesis of PEGylated PAMAM Precursor

The amounts of different components to be added are reported in Table 5 and were calculated as follows:
Amount of PAMAM dendrimer=20 mg
The ratio of PEG3000:Dendrimer=1:3.33
Amount of PEG3000 needed=(30/100)×20=6 mg
The ratio of PEG with NHS and EDC is 1:8:8, giving masse ratio 6 mg:48 mg:48 mg

TABLE 5

Amounts of different components for synthesis of PEGylated PAMAM precursor

| | Materials | CAS no | MW | State | Amount |
|---|---|---|---|---|---|
| NHS | N-hydroxysuccimide | 6066-82-6 | 115.09 | powder | 48 mg |
| EDC | 1-ethyl 3-(3-dimethyl amino-propyl)carbodiimide | 25952-53-8 | 119.70 | powder | 48 mg |
| PEG3000 | PEG polymer(MAL-PEG-COOH) | 948595-08-2 | MP 3000 | | 6 mg |
| G5 | PAMAM Dendrimer G5 | 163442-68-0 | 5912.32 | liquid | 20 mg |

The synthesis of PEGylated PAMAM precursor was performed by the following steps [Alibolandi et al, Int J Pharm. 2017 Mar. 15; 519 (1-2):352-364]:
1. PAMAM dendrimer was dissolved in PBS at pH 7.4
2. 6 mg PEG-COOH was added to the solution and mixed with NHS and EDC in the ratio of MAL-PEG-COOH: NHS:EDC 1:8:8
3. The mixture was stirred for 16 hours at 800 rpm, protected from light.
4. Dialysis was done (cut off: 14000 Da) against 3 mL of PBS pH 7.4 for 24 hours to remove unconjugated PEG and residual EDC/NHS.
5. SPEED VAC was used to reduce sample volume
6. Characterization was done by DLS and 1H-NMR.

NMR was used to characterize the conjugates upon the selected conjugation and after the purification by a 24 h long dialysis with a 10-20 MWKO membrane. The observed change in NMR signal confirmed the successful attachment of antigen in the preparation of the nanoconjugate complex.

2.4 Attachment of Antigen/Carbohydrate/Lipid to PEGylated PAMAM Precursor

The different components of the nanoconjugate complex may be attached to the backbone by different methods. A generalized description of different "attachment methods" is provided below as well as the step by step process for the synthesis of nanoconjugate complex no 1.

General noncovalent attachment protocol: In order to yield the target nanoconjugate in 1×PBS (1 mL), 10% excess of the required amount of components was added dropwise over 2 hours to a stirred solution of PEGylated dendrimer in 1×PBS (100 mM, pH 7.2, 2 mL). The reaction mixture was stirred for 24 hours and afterwards analyzed by 1H-NMR on Bruker 400 (DTU Chemistry, Denmark). The product has been concentrated using 10K dialysis kit from Thermo Fisher Scientific.

General click chemistry attachment protocol: A 10% excess of azide or alkyne reagents has been added to PEGylated PAMAM containing corresponding alkyne or azide groups in 100 mM TEAA buffer at pH 7.0 (2 mM solution PAMAM in 1 mL). Alkyne/azide containing PAMAM precursors are available from commercial supplies such as Sigma, or can be made together with attaching PEG using NHS-alkyne and NHS-azide reagents available from e.g. Lumiprobe (see example for nanoconjugate 1). The components that get clicked such as a peptide or a DNA sequence are obtained from commercial suppliers or synthesized in house, with including the desired alkyne or azide label for click chemistry. Afterwards copper-THPTA and freshly prepared ascorbic acid were added, and the resulting mixture was degassed by argon and kept at room temperature for 12 h. The resulting mixture was subjected to dialysis through 10K device (Thermo Fisher Scientific). The product was analyzed by 1H-NMR on Bruker 400 (DTU Chemistry).

General NHS chemistry attachment protocol: A 10% excess of NHS reagents has been added to PEGylated PAMAM containing free amino groups in 100 mM bicarbonate buffer pH 8.3 (2 mM solution PAMAM in 1 mL). The reaction was gently stirred at room temperature for 4 h and then subjected to dialysis through 10K device (Thermo Fisher Scientific). The product was analyzed by 1H-NMR on Bruker 400 (DTU Chemistry).

2.5 Step-by-Step Protocol for Synthesis of Nanoconjugate Complex No 1

The General Synthesis Strategy for Conjugate 1:
1. NHS-PEG coupling to G5 PAMAM, dialysis;
2. Coupling reaction with 3 equivalent heptanoic acid, dialysis;
3. Treatment of product of step (2) with Azide-PEG3-amine (Limiprobe, cat no. 218-1g);
4. Click chemistry of galactose-alkyne and oligonucleotide-alkyne mixture to the product of step (3) in a molar ratio 3:1.

Step 1. Same as described in section 1.3 "Synthesis of PEGylated PAMAM precursor", followed by dialysis using 10 kDa MWKO membrane (Thermo Fisher Scientific, cat no 87729) following the manufacturer's protocol.

Step 2. PEGylated G5 PAMAM prepared in step 1 was re-suspended in 100 mM PBS (pH 7.2), at concentration 1 mg/mL (1 mL). Heptanoic acid (6 µL of 10 mM stock in t-BuOH), and EDC (12 µL of 10 mM stock in DMFA) were added, and the reaction was kept at room temperature for 36 hours, at gentle stirring (200 rpm). The product was dialyzed using 14 kDa MWKO membrane (Thermo Fisher Scientific) for 24 h and restored in 1 mL 100 mM bicarbonate buffer, pH 8.2, for the step 3.

Step 3. A solution of step 2 product in 100 mM bicarbonate (pH 8.2) was incubated at room temperature for 2 h with N,N'-diisopropylcarbodiimide (7 µL; DIC, Sigma D125407) and N-hydroxysuccinimide (10 µL of 10 mM stock in milliQ water; Sigma (cat no 130672). Azide-PEG3-amine (15 µL of 10 mM stock in milliQ water; Lumiprobe, cat no. 218-1g) was added, and the reaction was kept at room temperature for 12 hrs at gentle stirring (200 rpm). The product was dialyzed using 14 kDa MWKO membrane (Thermo Fisher Scientific) for 24 h and restored in 200 µL 100 mM TEAA buffer, pH 7.2

Step 4. To a solution of step 3 product in 100 mM TEAA buffer (pH 7.2; 30 µL at concentration 1 mg/mL), the following reagents were subsequently added: DMSO (20 µL), D1-5'-hexynyl oligonucleotide (4.4 nmol hexynyl/TCCTTTCTTTCTTTCTT in 5 µL milliQ water; IDT), beta-Gal-TEG-Alkyne (8.8 nmol in 5 µL milliQ water; IDT, IRIS BIOTECH GBB1385), copper TBTA ligand (10 µL, 10 mM stock, Lumiprobe 21050) and freshly prepared ascorbic acid (5 µL of 25 mM stock in milliQ water; Sigma A92902-25G). The mixture was degassed by flushing with argon over 3 min and kept at room temperature on 200 rpm shaking for 48 hr. The product was dialyzed using 20 kDa MWKO membrane (Thermo Fisher Scientific) for 24 h and restored in 200 µL 100 mM PBS, pH 7.2.

Example 3: Solubility of Nanoconjugate Complex

Figure 3:
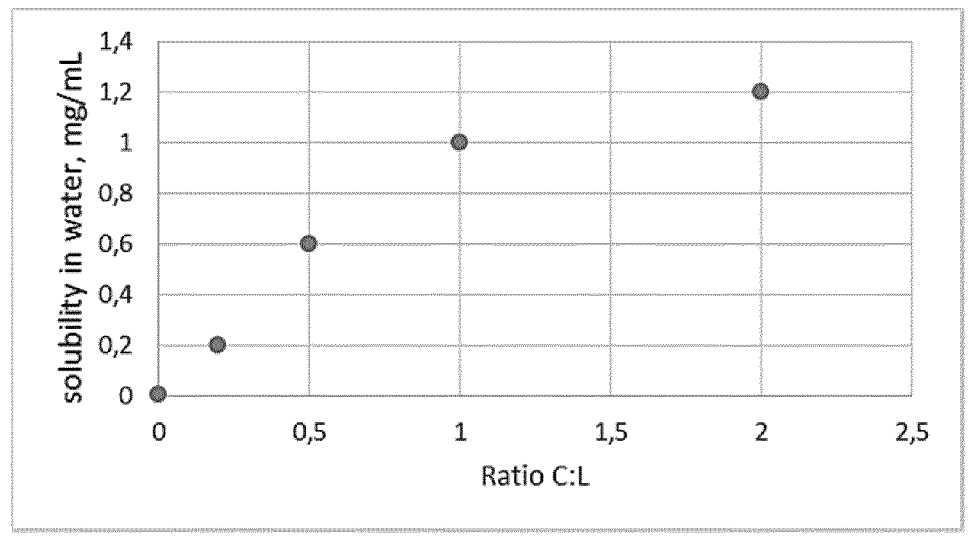
FIG. 3. Solubility of PAMAM (G5)-PEG coupled with varying ratios of lipid and carbohydrate.

The effect of a carbohydrate component on solubility of the nanoconjugate complex is demonstrated by a titration experiment, where an increasing amount of glycose is coupled to G5-PAMAM-PEG-butyric acid. 100 mM PBS buffer (1 mL, pH 7.2, Sigma) was added dropwise to the evaporated conjugate (1 mg). The solubility can be measured simply by filtering, drying and weighing the undissolved conjugate. FIG. 3 shows the solubility data for the conjugate, as a function of the amount of added carbohydrate component to the lipid. As seen in FIG. 3, the optimal ratio of carbohydrate:lipid (C:L/B) is approx. 1:1 or higher; the solubility drops dramatically if less than 1:1 C:L/B ratio is applied. Without any carbohydrate component present, only 0.01 mg of nanoconjugate complex gets dissolved in water, which is not suitable for therapeutic applications.

Example 4: Pyrogenicity and Complement Activation

Figure 4:
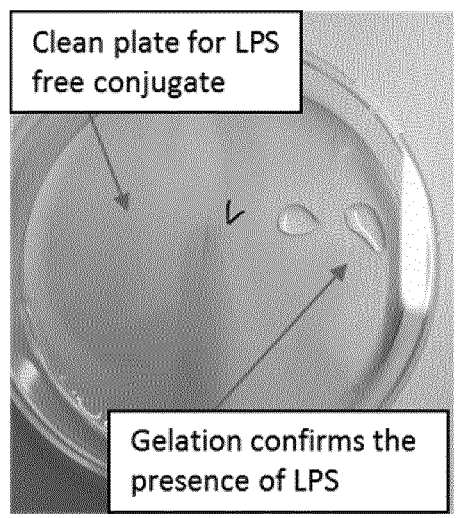
FIG. 4. LPS contamination test. Gelation on the right side (LPS standard) is not seen for the glucosamine conjugate (left side of a plate).
Figure 5:
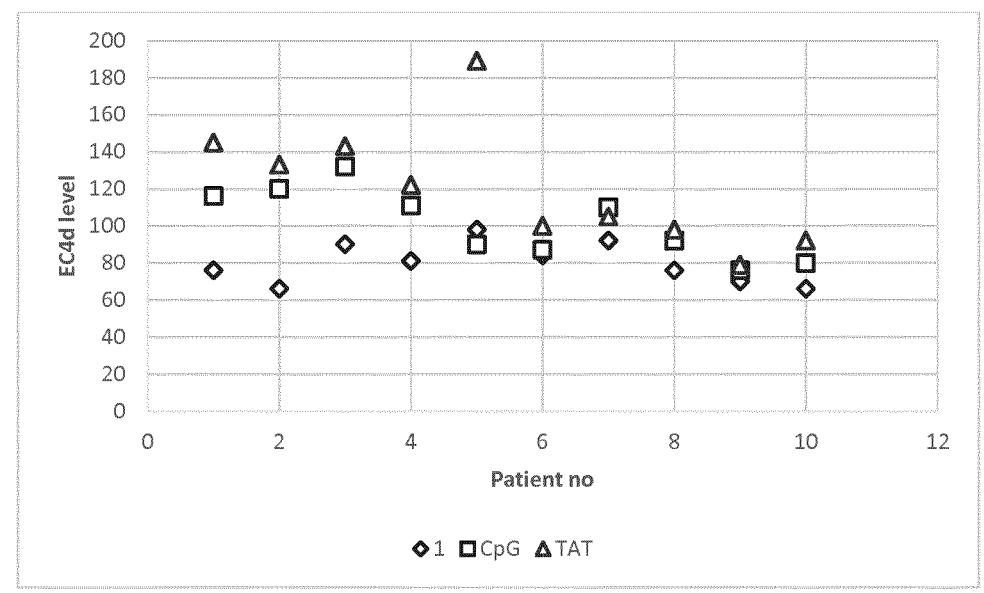
FIG. 5. Complement activation test: EC4d levels in healthy controls (patients no 6-10) and patients with kidney disease (patients no 1-5).

To evaluate pyrogenicity and complement activation that can interfere with the in vivo testing of the nanoconjugate complexes, standard procedures were used [Huang et al. Osteoarthritis Cartilage. 2016 October; 24(10): 1769-1775]. Pyrogenicity is most often caused by bacterial antigens such as lipopolysaccharide (LPS). Pyrogenicity was tested for the nanoconjugate complexes vs. commercial LPS standard in dilutions 1:100 down to 1:100,000, in fresh MQ water and laminar setting. The result confirms the absence of any contamination in the conjugates as all plates were "clean" for the conjugates of the present invention, while gelation was observed in the presence of LPS as a control (FIG. 4). Complement activation was tested in SLE positive human blood (Odense University Hospital, n=5), incubating the nanoconjugate complex no 1 (from Example 1) and controls (CpG oligonucleotide and TAT peptide), at 37° C. for 24 h., and measuring biomarkers (EC4d) for complement activation by standard ELISA. ELISA kits for this purpose are purchased from commercial suppliers, and the procedure suggested by the supplier is being followed. FIG. 5 shows EC4d levels in healthy controls (patients no 6-10) and patients with kidney autoimmune disease (patients no 1-5); demonstrating no increase in EC4d levels in kidney auto immune disease patients compared to healthy controls, hence no complement activation in 24 h for nanoconjugate complex no 1, compared to CpG and TAT.

Example 5: Stability of Nanoconjugate Complexes: Oxidation, Storage and Aggregation The solution of a nanoconjugate or a control in 100 mM PBS (pH 7.2, Sigma), at concentration 1 mg/mL was stored at −20° C. or +4° C. Aliquots were taken every month. To evaluate for aggregation, supernatant samples were analyzed by measuring optical density at 260 (DNA antigens)/280 nm (peptide antigens). A decrease in optical density >15% was considered as an aggregation. Oxidation was tested by HRMS, comparing the mass of initial compound to the sample. Increased mass by m/z 32 and more confirmed the oxidation. Chemical composition was tested in LC MS, elution system isocratic gradient tBuOH in PBS buffer 10→90%, flow speed 1 ml/min, on C18 analytical column, connected to the MS spectrometer. The mass of a sample was compared to the initial compound used as a control. Deviation in the LC profile and MS >15% was considered a decomposition. The results are reported in Table 6.

TABLE 4

Stability studies of nanoconjugates 1-5 to oxidation and storage analyzed by HRMS and to aggregation studied by LC MS.

| Compound no. | Oxidation stability −20° C., months | Storage at −20° C., months | Storage at +4° C., months | Aggregation −20/+4° C., % |
|---|---|---|---|---|
| 1 | >12 | >12 | >12 | <5/<5 |
| 2 | 8 | >12 | 4 | 7/<5 |
| 3 | 7 | >12 | 6 | 11/<5 |
| 4 | >12 | 7 | 4 | 25/14 |
| 5 | >12 | 8 | 4 | 30/22 |

Example 6: Toxicity Study

All the antigens and nanoconjugates selected by rational design have been tested in terms of cellular toxicity; this includes all the nanoconjugates shown in Table 2. Conjugates 1-5 were tested using IL-19 and KIM-1 biomarkers in cell lines and in vivo. Conjugates 6-10 were tested in human blood using viability assay, see below.

Apparent toxicity is sequence dependent and requires careful design and testing of the selected antigens and helper molecules. Cell line tests were performed to ensure ethically reasonable transfer of the conjugate from bench to animal model. BHK cells were selected due to robustness and low cost. BHK (baby hamster kidney) cells (BHK-21 [C-13] ATCC® CCL-10™, USA) were grown in MEM medium (BioWhittaker, USA). Complete medium for BHK cells is MEM+2 mM L-glutamine (Sigma Denmark, 1294808); +5% fetal bovine serum (Sigma F2442). Cells were grown in a humidified, 37° C., 5% CO2 incubator and split three times at 1:5, reaching 90% confluency. Cell growing took 11 days in total. A solution of nanoconjugate complex at concentration 1 nM or 10 nM was added to cells in 1×PBS and incubated for 24 h. Afterwards the cells were fixed with MeOH (Sigma, cell culture grade), crashed and subjected to analysis of IL-19 using commercial ELISA kits (The Quantikine human IL 19 kit, R&D Products, USA), following manufacturers protocols. The results are shown in Table 7.

TABLE 5

Toxicity study of nanoconjugate in BHK cell line and in vivo (NZB/W, IV administration, 10 nM; blood sample analyzed 36 h after initial administration).

| Compound no. | BHK: IL-19, pg/mL (cell lysate) | NZB/W: IL-19, pg/mL (plasma) | NZB/W: KIM-1, ng/mL (plasma) |
|---|---|---|---|
| 1 | 88 | 76 | 1.4 |
| 2 | 75 | 95 | 2.2 |
| 3 | 94 | 104 | 3.1 |
| 4 | 122 | 170 | 2.4 |
| 5 | 134 | 211 | 5.2 |
| Negative control* | na | 73 | 1.4 |
| Gentamicin treatment | na | 78 | 2.05 |

*Healthy mice;
na = not applied

As it is shown in Table 7, no apparent toxicity was detected in the analysis using BHK cells, measuring the levels of IL-19 which is a biomarker for toxicity. When synthetic peptide TAT (positive control for toxicity in cellular assays) was added, the IL-19 levels did increase (data not shown). Since all levels were within the normal range (70-150 μg/mL), confirming no apparent toxicity of the conjugates, the conjugates were then tested in the NZB/W mice.

Nine-week-old NZB/W mice were kindly provided by Heegaard group, Statens Serum Institute, Denmark; ten mice (all females) were kept in sterile boxes covered by a filter and fed sterile water and food. The mice were grown for 10 weeks and reached weight 17-19 g in average. The mice were bled before the experiment to check for the presence of anti-dsDNA antibodies (a-dsDNA) by standard ELISA. Only those with a-dsDNA in titer 1:1000-1:12000 were used for this study. The nanoconjugate complexes were added to the tail vein. Nanoconjugate complex was administrated using IV in 1×PBS, applying the nanoconjugate complex at 160 μg/kg animal weight for 10 nM concentration. Blood samples were withdrawn 36 hours after initial administration and subjected to analysis of IL-19 and KIM-1 using commercial ELISA kits (The Quantikine human IL 19 kit, R&D Products, USA; KIM 1 ELISA kit ADI-900-226-0001, ENZO Life Sciences, USA), following manufacturers protocols. These results are also shown in Table 5.

Based on the stability and toxicity studies, nanoconjugate complex no 1 was selected as the most potent candidate and studied further in vivo.

Example 7: In Vivo Mice Assay

For the further in vivo test, a well-described mice model was selected: NZB/W mice, these have been used as a model for autoimmune disease since the early 1960s. Mice of this hybrid cross develop an autoimmune disease resembling human SLE.

Nine-week-old NZB/W mice were kindly provided by Heegaard group, Statens Serum Institute, Denmark; they were grown and tested for the presence of anti-dsDNA antibodies as described in example 6. Nanoconjugate complex was added to the tail vein, administrated using IV in 1×PBS, applying the nanoconjugate complex at 160 μg/kg animal weight for 10 nM concentration, and 16 μg/kg animal weight for 1 nM concentration. Two mice were used for each conjugate. Mice received IV conjugate/control administration (same amount each time), with 12 h intervals for 5 days, and afterwards giving the same dose with 3 day interval over 3 weeks. Treatment with Gentamicin was used in control animals of same strain and age, at dosage 10 mg/kg animal weight and 1 mg/kg for final 10 nM and 1 nM administration, respectively. Administration regimen for same as for nanoconjugate complexes: IV in tail vein with 12 h interval for 5 days, and afterwards giving the same dose with 3 day interval.

Blood samples were withdrawn at time points: 24 h, 48 h, 1 week, 4 weeks after the beginning of each treatment. Plasma was centrifuged using Qiagen blood storage tubes and stored at −20° C. prior to analyses. ELISA analysis was performed using manufacturer's protocols in sera dilution 1:100 to 1:500. The results for nanoconjugate complex 1 are presented in FIG. 6. Conjugate at 10 nM and 1 nM administration reduces the disease activity index (DAI) over a month period, whereas control induces only a short term drop in DAI. At early time points 10 nM conjugate works better than 1 nM. However over a month the DAI falls similarly for both 1 nM and 10 nM conjugate, ending with DAI 5 vs. 22 in the beginning of a treatment (78% decrease in DAI).

Figure 6:
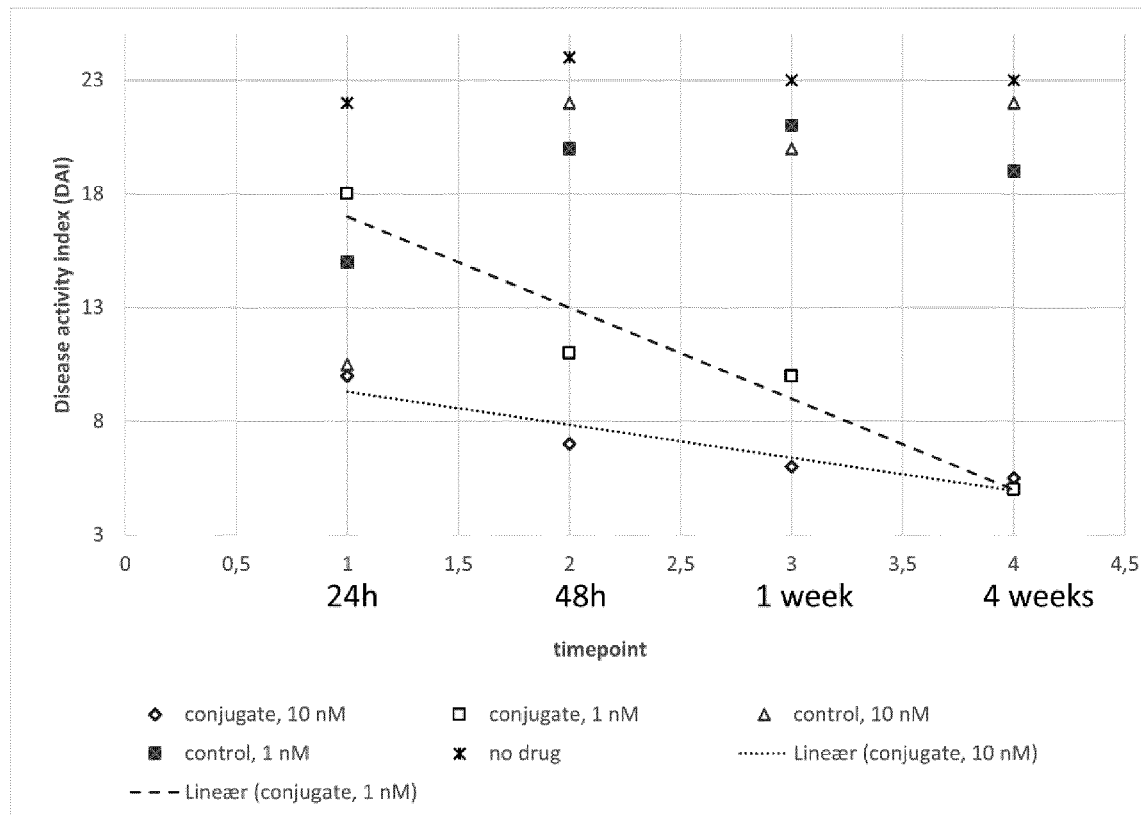
FIG. 6. Therapeutic effect of nanoconjugate complex 1 in vivo. Control=gentamicin FIG. 7. Cell viability upon adding nanoconjugate complexes 1, 6, 7, 8, 9, and 10

Since there are no spikes in the disease activity index that could be caused by complement activation, the data in FIG. 6, further indirectly confirms the lack of complement activation by conjugates, which would cause DAI raise.

Example 8: Interaction of Nanoconjugate Complexes with Human Primary Blood Cells Cytotoxicity and uptake by blood cells are all potential issues for the nanoconjugates. This was studied by FACS (fluorescence-activated cell sorting) using primary human blood cells and conjugates 1 and 6-10 (table 2), along with a G5 PAMAM control. To run FACS, the nanoconjugate complexes and the control were additionally labelled with CY5.5 NHS reagent (Lumiprobe), following this protocol: Conjugates 1,6-10 at concentration 1 mg/mL in 100 μL bicarbonate (0.1 M, pH 8.3) were added to 20 μl 10 mM dye stock in the DMSO. The mixture was stirred at 300 rpm in dark overnight and afterwards dialyzed at 10 KDa MWKO (Thermofisher dialysis cassette Cat no 87729), following the manufacturer's procedure. The conjugate was kept in 100 mM PBS at pH 7.2 afterwards.

For FACS experiments, fresh whole blood from five donors (Stanford University Hospital) was used. The protocol for the blood work up and incubation with conjugates is given below.
1. Pool together the blood from the 2 heparin tubes (total~20 ml)
2. Add 20 ml commercially available RPMI buffer (no FBS) (Sigma R0883)
3. 1600 rpm, 5 min, discard top pink layer
4. Repeat step 2-3 twice
5. Aliquot 250 ul of blood to each FACS tube.
6. Lyse with 3 ml of ACK lysis buffer (Gibco #A10492-01) for 10 mins, RT.
7. 1600 rpm, 5 min, discard supernatant
8. Wash twice with 2 ml RPMI buffer.
9. Resuspend with 250 ul RPMI buffer
10. Count cells. Take 5 ul of cells and add 95 ul Trypan blue.
11. Add 250 ul of designated conjugate prepared in RPMI buffer to each of the tubes (250 ul of 20 nM)
12. Mix cells with nanotubes by vortexing three times 5 counts each.
13. Incubate for 30 mins in 37° C. Caps are kept loose to keep cells alive.
14. Stop incubation by transferring tubes to ice for 20 min
15. Add 2 ml RPMI buffer, 1600 rpm, 5 min, discard supernatant
16. Repeat step 12.
17. Resuspend cell pellet in 100 ul of milliQ aqua solution (LD aqua diluted 1:1000 PBS), 10 minutes at room temperature, covered with foil.
18. Wash with FACS buffer, (for washes if using BD FACS tubes use 500 ul for each wash) Spin 5 minutes, 1500 rpm and remove supernatant. FACS buffer was 2% calf serum (Sigma 12133C), 1 mM EDTA, 0.1% sodium azide.
19. Resuspend pellet in 100 ul blocking buffer*(5% heat inactivated AB serum and 5% goat serum in PBS (Sigma P4417)))
20. Incubate on ice for 15 min
21. Add antibody CD20 (CD20 antibody (0.N.85): sc-70582, Santa Cruz Biotechnology) and HLADR (Anti-HLA-DR antibodies, human (clone: AC122), Miltenyi Biotec) directly to cells (2 ul for each antibody/100 ul of cell suspension).
22. Incubate on ice, 30 min
23. spin 1500 rpm 5 min 4° C.
24. Fix cells by re-suspending pellet in 200 ul of BD cytofix solution (BD 554714). Add Cytofix solution slowly to the cell pellet while vortexing or with frequent vortexing. Incubate at RT in the dark for 20-30 mins.

25. Wash with 500 ul of FACs buffer and re-suspend in 200 ul of FACS buffer.
26. Keep at 4C, avoid light till analysis (within 24 h)

The resulting samples were analyzed on BD FACS instrument (BD FACSLyric™). The results for specific cellular uptake are given in Table 8.

TABLE 6

Fluorescence intensity in cell population for each nanoconjugate complex and controls

| Conjugate | T cell | B cell | monocytes | NK | Neutrophils |
|---|---|---|---|---|---|
| G5 (control) | 11 | 21 | 5 | 24 | 35 |
| 1 | 8 | 10 | 6 | 16 | 20 |
| 6 | 5 | 12 | 11 | 18 | 37 |
| 7 | 14 | 32 | 30 | 21 | 12 |
| 8 | 11 | 20 | 35 | 24 | 8 |
| 9 | 14 | 12 | 30 | 21 | 60 |
| 10 | 11 | 18 | 35 | 24 | 76 |
| Cy5.5-RNA negative control | 2 | 1 | 1 | 4 | 2 |

Table 8 shows that PEGylated G5 PAMAM dendrimer (control) is being mostly taken up by neutrophils, and less by NK, T, and B cells, while monocytes take up only a little of G5. When the oligonucleotide, carbohydrate and lipid are added (conjugate 1), levels for all cells are somewhat similar to G5 alone, whereas removing the lipid part (conjugate 6) increases the uptake by neutrophils. For histone peptides (conjugates 7-10) the effect of lipid becomes dramatic. The uptake is high when the lipid is absent (conjugates 9-10), by neutrophils mostly, and it drops down to 8-12 in presence of the lipid (conjugates 7-8).

This data suggests three important facts: (1) T cells, B cells and monocytes are little affected by the conjugates. This means no activation and confirms low cytotoxicity/side effects for the therapeutics; (2) Peptide-containing therapeutics have higher uptake by monocytes than DNA conjugates, however T and B cells are still little affected; (3) Lipidation can be used as an instrument to fine tune the uptake intensity by neutrophils, especially for peptide-containing conjugates. This is of tremendous importance for drug delivery in e.g. rheumatoid arthritis. This finding also suggests a positive effect of lipidation on the bio-distribution given that the goal is to keep the therapeutic in the blood stream.

Example 9: Cell Viability Upon Adding the Conjugates

Figure 7:
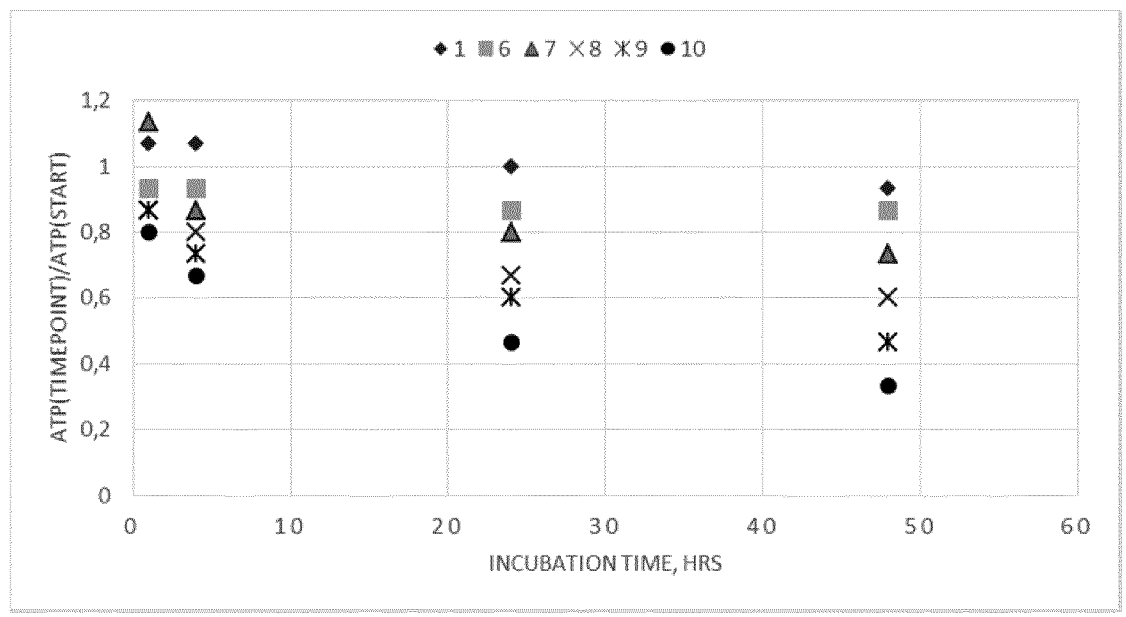

Cell viability upon adding the conjugates was assessed using Abcam luminescence kit (ab65314 Bioluminescent). The procedure for the assay was performed according to the manufacturer's protocol. Abcam's Cell Viability Assay Kit ab65314 (Bioluminescent) utilizes bioluminescent detection of the ATP levels for a rapid screening of apoptosis and cell proliferation simultaneously in mammalian cells. The assay utilizes luciferase to catalyze the formation of light from ATP and luciferin, and the light can be measured using a luminometer or Beta Counter. The assay is fully automatic for high throughput (10 seconds/sample). The microtiter plates containing incubation reactions for primary cells with nanoconjugate complexes were analyzed. The initial ATP concentration (before adding conjugate) was 0.15 pM±4%. Cell viability was monitored as low to no change in ATP concentration per well, given in FIG. 7 (used Magellan Tecan microplate sunrise reader). The principle for the detection is: ATP+luciferase+luciferin→visible light (detected by plate reader), hence more ATP=more light (for details, see kit manual (ab65314 Bioluminescent)). Positive control: DAPI at concentration 1 mg/mL in 15% DMSO-1×PBS (10236276001 Roche). For DAPI, drop in ATP level from the initial concentration reached 26-fold at 48 h time point.

The obtained values for conjugates were compared to the data for cells without adding anything and to DAPI data as no toxicity and high toxicity, respectively. Low values of cell viability means high toxicity and vice versa. From the cell viability assay it was found that primary human cells are only little affected by adding conjugates (conjugates vs. DAPI), even in the presence of potentially toxic peptides in the conjugate structure. It was also seen that the lipidation has a positive effect on the viability for conjugates 7, 8 vs 9, 10, at later time point 48 hr.

Example 10: Synthesis of Labelled PAMAM Nanoparticles

Step 1. Labelling of PAMAM with Sulfo-Cy5.5.

At the first step, PAMAM G5 was labelled with sulfo-Cy5.5 NHS reagent. Stock solution of the sulfo-Cy5.5 NHS in DMSO (10 mM; 0.5 μL) was added to the solution of the PAMAM/G5 precursor (1 nmol) in 100 mM bicarbonate buffer, pH 8.3 (200 μL). The reaction was kept in dark overnight and purified by dialysis against 20K membrane 2×500 mL mQ, 1 h, and overnight (500 mL MQ).

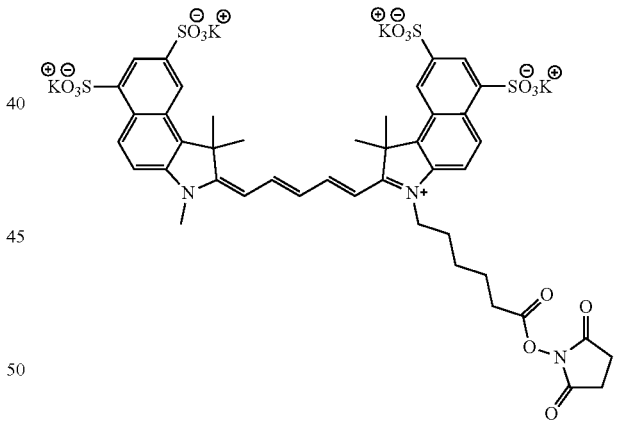

Chemical structure of sulfo-Cyanine 5.5 NHS ester used in step 1.

Step 2. N-hydroxysuccinimide (15 mM; 100 ul) was incubated with PEG5000 COOH (10 mM; 100 ul), and/or lipid/carbohydrate reagent (10 mM; 100 ul), in MQ water:DMFA 4:1, v/v, over 3 h. The resulting solution was added to 1 mM G5 PAMAM in 1× bicarbonate buffer (pH 8.2; 200 ul), in presence of 15 mM DIC. Both the labelled dendrimer from step 1 and its unlabeled precursors were reacted in separate experiments. The reaction was kept at room temperature under shaking (300 rpm) overnight, and the product was purified by the dialysis against 10K membrane 2×500 mL MQ, and overnight (500 mL MQ).

Step 3. Amide Coupling with Peptide Antigen

The coupling was performed as described by Valeur et al., Chem Soc Rev Vol. 38 (2009) pp 606-631. A desired peptide (20 nmol in 300 μL DMSO) was incubated with DCC (30 nmol) and HOBt (30 nmol) for 1 h at room temperature. The resulting mixture was added to the product of step 2 (1 nmol in 200 μL mQ), and the reaction was kept for 2 hr at room temperature, under 250 rpm shaking. The product was purified by the dialysis against 14K membrane using 2×500 mL MQ, and overnight (500 mL MQ).

The products were analysed by gel electrophoresis, UV-vis absorbance and fluorescence as described below. Concentration of PAMAM in the product was determined by OD255 at pH 8.2. The nanoparticles were characterized by DLS and SEM.

Example 11: Synthesis of Labelled Chitosan-Hyaluronic Acid (CS-HA) Nanoparticles In this study the attachment of antigens was done non-covalently owing to high complexation activity of the CS-HA nanoparticle. Lipid and carbohydrate were not added to the complex for this study, since CS and HA are carbohydrates themselves, and because coupling of the lipid was not efficient at the accepted pH range for CS-HA complex.

Step 1. Encapsulation of DNA/RNA and/or Peptide Antigens

At pH 6.5, 0.069% w. chitosan (120 kDa) was dissolved in 2 mL 1×PBS, and DNA/RNA (1.2 nmol) and/or peptide (1.2 nmol). The mixture was kept under stirring 1000 rpm for 10 min. The product was purified with Amicon filter device of MWKO 5 kDa following manufacturer's protocol. The product was reconstituted in 2 mL 1×PBS, pH 6.5.

Step 2. Labelling and PEGylation of Hyaluronic Acid

Hyaluronic acid (0.15 mg/mL; 10 kDa) was dissolved in 1.7 mL mQ water, and NHS (0.6 μmol, 10 μL of 6.9 mg/mL fresh stock in water) was added. The mixture was stirred overnight at 1000 rpm, and afterwards 1× bicarbonate (pH 8.0; 200 μL), methoxy-PEG-amine (0.3 μmol; Polysciences, 26026-1) and/or sulfo-Cy5.5 amine (0.3 μmol; Lumiprobe) were added, in a total volume of 2.3 mL. The reaction was stirred at room temperature, 1000 rpm, in dark, overnight, and worked up using Amicon 10 kDa MWKO, following the manufacturer's protocol. The product was reconstituted in 2 mL 1×PBS, pH 5. The sulfo-Cy5.5 labelled product should not be heated and may not be exposed to light.

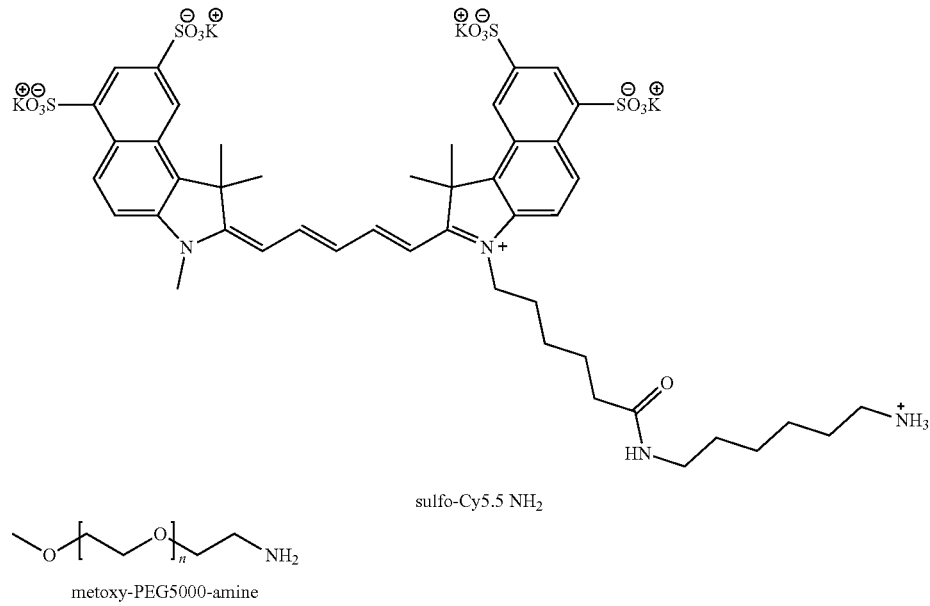

sulfo-Cy5.5 NH₂ metoxy-PEG5000-amine

Chemical structures of sulfo-Cy5.5 amine and methoxy-PEG5000-amine reagents.

Step 3. Complexation of Chitosan with Hyaluronic Acid

The product of step 1 (1 mL) was mixed with the product of step 2 (1 mL) in the buffers mentioned above. The mixture was kept under 1000 rpm shaking, room temperature, for 30 min, and purified by 50 kDa MWKO Amicon, following the manufacturer's protocol.

The nanoparticles were characterized by DLS and SEM.

Example 12: SLE Mice Study

The CS-HA-PEG5000-D1 nanoconjugate complex (synthesized as described in example 11) was tested in NZB/W F1 mice: CS-HA-PEG5000-D1 in 1×PBS was administered by IV in the tail vain every 12 h over 2 weeks, at a conjugate dosage of 160 μg/kg animal weight for 10 nM concentration. 30 mice were tested; 80% were female; average age 20 week; average weight/median 20.2 g (18.4 g-23.1 g). Hydroquinone (HQ) was used as control, PO, 2 mg/kg, every 24 h over 2 weeks.

Figure 8A:
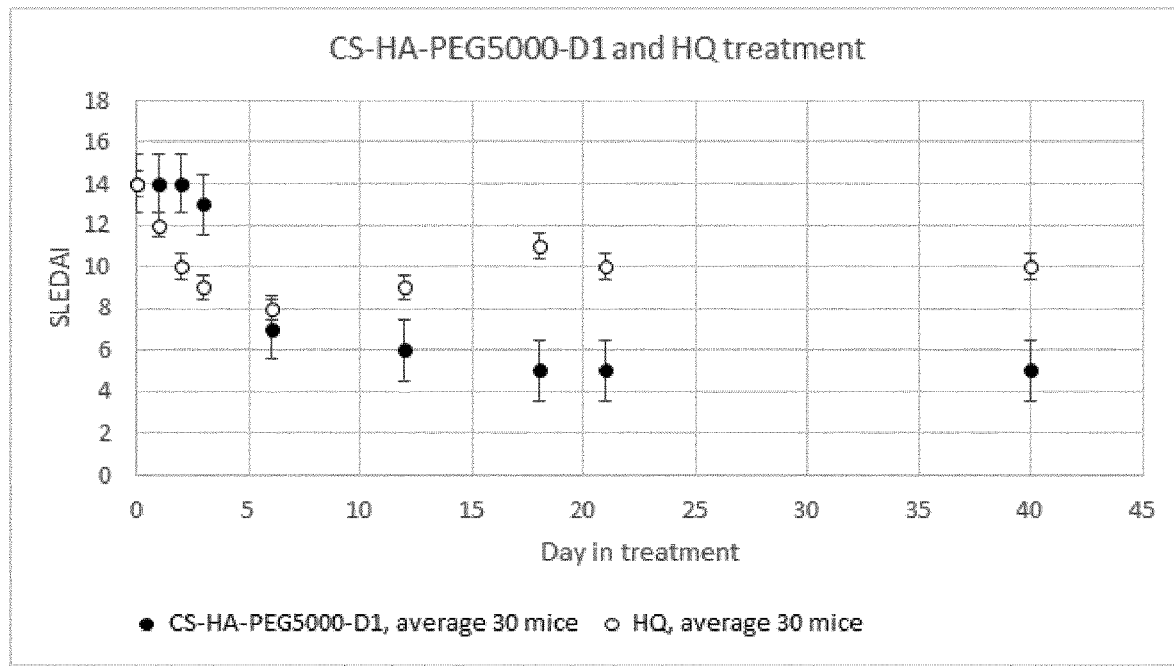
FIG. 8. A) SLEDAI (SLE disease activity index) for mice treated with v nanoconjugate complex treatment and HQ control are shown as hallow and bold circle, respectively. B) CS-HA-PEG5000-D1 control in healthy mice.

FIG. 8A shows the SLEDAI (SLE disease activity index) for the mice treated with CS-HA-PEG5000-D1 nanoconjugate complex treatment compared tp the HQ control are shown as hallow and bold circle, respectively. HQ treatment reduces SLEDAI faster; however the disease flares after day 17 in treatment.

CS-HA-PEG5000-D1 gives a more stable reduction in SLEDAI over the entire treatment course and maintains low SLEDAI levels 2 weeks after.

Figure 8B:
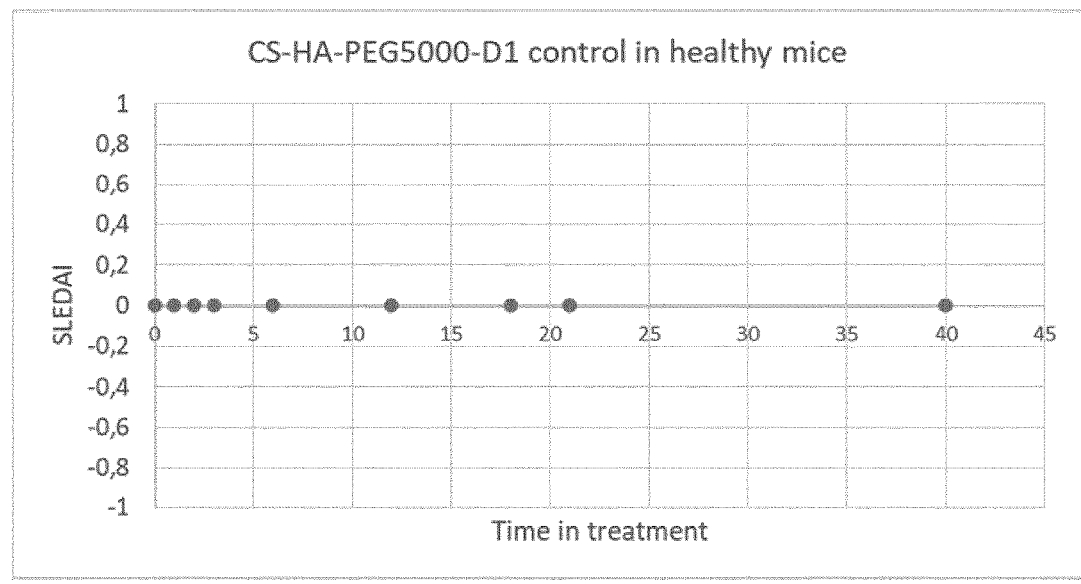

As a control, 20 healthy mice (controls; KO) were treated with the CS-HA-PEG5000-D1 complex; same regimen as described above. Results are presented in FIG. 8B, confirming no DAI levels.

Example 13: Selectivity of Antigens D7 and D8

The goal was to purify disease associated antibodies using synthetic antigens; and further study selectivity of the antigens.

Synthetic antigens D7 and D8 (see table 9) were synthesized and their selectivity tested.

TABLE 9

Synthetic CKD antigens

| Component | Antigen sequence |
|---|---|
| D7 | Pre-annealed amino-modified oligosaccharide: $NH_2$-$(ATCG)_6$:$(TAGC)_6$ (SEQ ID NO. 7) |
| D8 | Pre-annealed amino-modified oligosaccharide: $NH_2$-$(TCCT)_6$:$(AGGA)_6$ (SEQ ID NO. 8) |

SLE antibodies from sera were captured by affinity chromatography using NHS-sepharose and modified antigens as specified in table 9. The protocol of GE Life Science, gravity affinity purification of antibodies, was followed: Column was packed with sepharose, and washed with 0.01% cold HCl; 2 mg/ml ds antigen in 0.1M bicarbonate pH>8 was added; incubated for 1 hour; wash with 10-column volumes NaOAc; wash with 5-10 column volumes 50 mM phosphate buffer pH 7. Sera was pre-treated with $CaCl_2$/dextran to remove lipoproteins prior to applying to column. Sera sample was added to column; incubated for 4 min; washed at 0.5 ml/min flow rate with 20 mM PBS, 5 column volumes; and finally SLE antibodies were eluted with 3 column volumes of 100 mM glycine-HCl, 10% dioxane pH 2.5-3.

Standard ELISA was used to test the selectivity of D7 and D8. ELISA plates comprising antigens D7 and D8, respectively, were tested for their ability to specifically bind the purified SLE-antibodies compared to control samples comprising other antibodies. It was found that especially D8 is selective for SLE antibodies, while D7 was not.

Example 14: Screening of RA Cit-PEP Library

In autoimmune diseases, epitope-antibody complexes are potent interactions to trigger the specific uptake of a drug. ACPA in particular are intriguing receptors to enter RA associated immune cells. The initial goal was therefore to identify an effective citrullinated peptide epitope for targeting RA associated cells. Table 10 shows the selected twenty-five peptide sequences that have been screened in this work.

TABLE 10

Citrullinated peptide epitopes

| PEP # | Sequence | Protein origin* | Comments |
|---|---|---|---|
| 1 | HHP GIA EFP S(Cit)G KSS SYS KQF (SEQ ID No 9) | fib | |
| 2 | HHP GIA EFP S(Cit)G KSY SYS KQF (SEQ ID No 10) | fib | Mutated PEP1 |
| 3 | HGP GIA EFP S(Cit)G PSY SYS KQF (SEQ ID No 11) | fib | Mutated PEP1 |
| 4 | HGI GLA EFP S(Cit)G KIS AYS KQF (SEQ ID No 12) | fib | Mutated PEP1 |
| 5 | HGP GGA EFP S(Cit)G KAY SYG KQF (SEQ ID No 13) | fib | Mutated PEP1 |
| 6 | AEGGGV(Cit)GPRVVE (SEQ ID No 14) | fib | |
| 7 | ASSGGV(Cit)GPRIVE (SEQ ID No 15) | fib | Mutated PEP6 |
| 8 | AEGASV(Cit)GPRVVE (SEQ ID No 16) | fib | Mutated PEP6 |
| 9 | KDLLPS(Cit)D(Cit)QHLPLIK (SEQ ID No 17) | fib | |
| 10 | KDLLPS(Cit)DGQHLPLIK (SEQ ID No 18) | fib | Mutated PEP9 |
| 11 | KDLLPS(Cit)D(Cit)GAIPLIK (SEQ ID No 19) | fib | Mutated PEP9 |
| 12 | QMRMELE(Cit)PGGNEIT(Cit)GGSTSYG (SEQ ID No 20) | fib | |
| 13 | NVSPGT(Cit)(Cit)EYHTEK (SEQ ID No 21) | fib | |

TABLE 10-continued

Citrullinated peptide epitopes

| PEP # | Sequence | Protein origin* | Comments |
|---|---|---|---|
| 14 | NVAYPT(Cit)(Cit)EYHGEK (SEQ ID No 22) | fib | Mutated PEP13 |
| 15 | ST(Cit)SVSSSSY(Cit)(Cit)MFGG (SEQ ID No 23) | vim | |
| 16 | AAPVSGSSY(Cit)(Cit)MFGG (SEQ ID No 24) | vim | Mutated PEP15 |
| 17 | ST(Cit)SVSSSSYKGAFLG (SEQ ID No 25) | vim | Mutated PEP15 |
| 18 | VYAT(Cit)SSAV(Cit)L(Cit)SSVP (SEQ ID No 26) | vim | |
| 19 | VYATYGSAV(Cit)L(Cit)SSVP (SEQ ID No 27) | vim | Mutated PEP18 |
| 20 | VYAT(Cit)SSAVGLGSSVP (SEQ ID No 28) | vim | Mutated PEP18 |
| 21 | A(Cit)TKQTA(Cit)KSTGGKAP (SEQ ID No 29) | His | Citrullinated fragment of human histone 3 |
| 22 | AA(Cit)KSAPSTGGVKKPH (SEQ ID No 30) | His | Citrullinated fragment of human histone 3 |
| 23 | Y(Cit)PGTVAL(Cit)EIKKYQKS (SEQ ID No 31) | His | Citrullinated fragment of human histone 3 |
| 24 | LI(Cit)KLPFQ(Cit)LV(Cit)EIAQDFK (SEQ ID No 32) | His | Citrullinated fragment of human histone 3 |
| 25 | LCAIHAK(Cit)VTIMPKDI (SEQ ID No 33) | His | Citrullinated fragment of human histone 3 |

*fib = fibrinogen; vim = vimentin; His = histone.

The citrullinated peptides epitopes belonged to three major groups, based on the protein they were derived from: fibrinogen (PEP1-PEP14), vimentin (PEP15-PEP20) and histone 3 (PEP21-PEP25) derived peptides. The rationale behind selecting the peptides has been the reported sequences and confirmed activity in RA. Vimentin and fibrinogen are often mutated among individuals. To take this into account, the mutated sequence variants for fibrinogen and vimentin have been recognised using BSI SPIDER homology search software.

Figure 9:
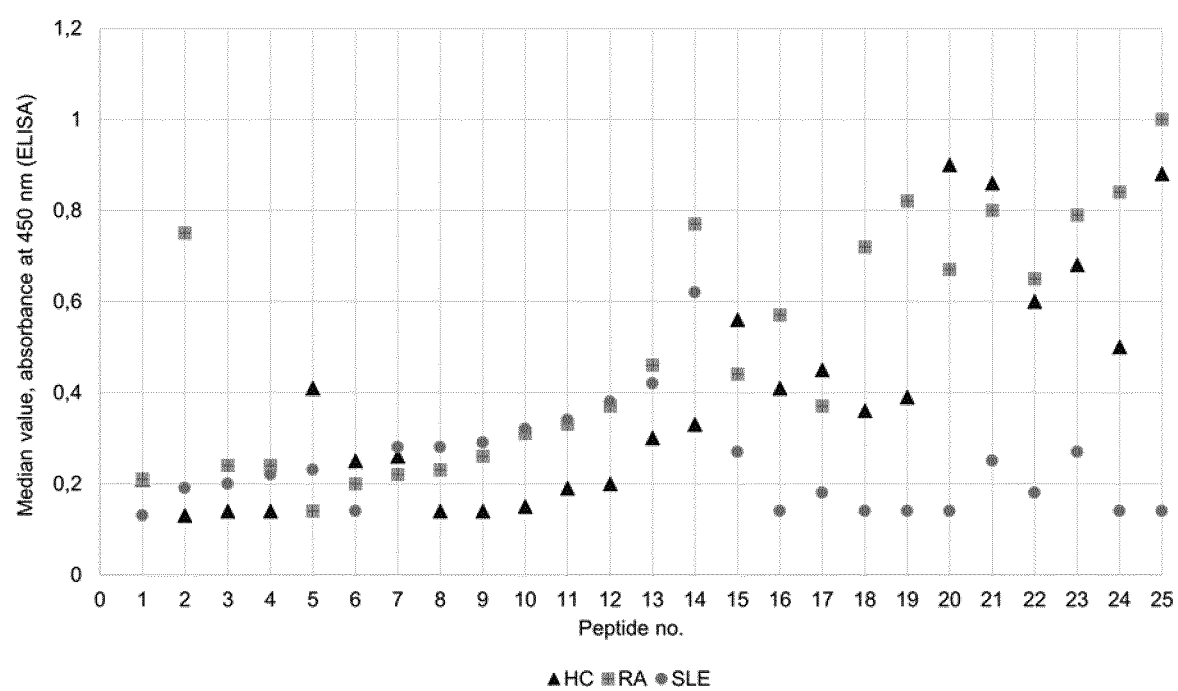
FIG. 9: ELISA screening of citrullinated peptide antigens PEP1-PEP25 (SEQ ID No 9-33); a cohort of 30 RA patients, 30 matched healthy controls and 30 patients with systemic lupus erythematosus.

Citrullinated peptide antigens PEP1-PEP25 (SEQ ID No 9-33) (free amine and carboxy-termini) have been purchased from CALSO, Copenhagen, Denmark, and screened in ELISA of a cohort of 30 RA patients, 30 matched healthy controls and 30 patients with systemic lupus erythematosus. The results are shown in FIG. 9. Overall, 16 peptide antigens (53%), from all the three groups, recognised RA sera. However, histone 3 derived PEP21-PEP25 showed elevated signal in 17-23% healthy controls. Multiple fibrinogen derived peptides showed high recognition rate of RA sera but also of a control disease SLE (10-57% and 7-23%), whereas vimentin peptides had lower binding levels in RA (23-30%).

Next, we compared mutated fibrinogen and vimentin epitopes to native proteins. Prior to ELISA, the mutated epitopes had been confirmed as homologs to the native proteins in NCBI BLAST, with identity score 90-100%. In ELISA, especially mutations in fibrinogen epitopes had a great effect on antibody recognition. On the contrary, mutations in vimentin epitopes had minor to no effect on ACPA binding levels. To the best of our knowledge, this is the first report showing the high influence of mutations within fibrinogen epitopes on ACPA binding. Last, BSI identified no mutants in histone 3 derived sequences, which is in agreement with the fact that histones are highly conservative proteins that rarely mutate.

Among all tested peptide epitopes, PEP2 with a sequence HHP GIA EFP S(Cit)G KSY SYS KQF (Cit=citrullin) demonstrated a high binding in RA samples (57%), and low to no binding in healthy controls and SLE (0% and 7%). This is in line with previous reports suggesting high relevance of citrullinated fibrinogen to RA.

Example 15: Preparation of PEP2-Nanoconjugates: Chitosan/Hyaluronic Acid/PEG/PEP2

I) Covalent Attachment of Peptide Via PEG to CS/HA

Peptide antigen was modified on solid support via C end with COOH-PEG-NH2Fmoc. Fmoc group on PEP2 was deprotected following standard protocol using 20% Piperidine in DMF.

Covalent conjugation of Hyaluronic acid and PEG-PEP2 product was done via amide bond on PEG. In doing this, 0.5 mg of PEP2-PEG NH2 was coupled with 1 mg Hyaluronic acid at pH 8.3 via NHS/EDC coupling reaction, using 1 mg NHS and 1.3 mg EDC. The mixture was stirred for 6 hrs at 800 rpm. Then, the product was purified with Amicon filter device of Molecular Weight Cut Off (MWCF) 5 kDa following standard protocol for removing residues of NHS/EDC and unconjugated PEG-PEP2. The characterisation of complex was done by MALDI MS and UV VIS. MALDI results showed no peaks of peg peptide followed by absorbance peak of peptide in UV VIS at 280 nm which showed the covalent conjugation of peg peptide with Hyaluronic acid.

The obtained covalent complex PEP2-PEG-HA was mixed with 3 mg of Chitosan for 1 hr, at 800 rpm. The reaction was quenched with 0.01 M Glycine for 10 min. Samples were then analysed by Nanosight and SEM, given below.

II) Non-Covalent Attachment of Peptide to CS/HA

Step 1. Encapsulation of PEP2: At pH 6.5, 0.069% w. chitosan has been dissolved in 2 mL 1×PBS, and PEP2 (1.2 nmol) has been added. The mixture was kept under stirring 1000 rpm for 10 min. The product was purified with Amicon filter device of MWKO 5 kDa following manufacturer's protocol. The product has been reconstituted in 2 mL 1×PBS, pH 6.5.

Step 2. Labelling and PEGylation of hyaluronic acid: Hyaluronic acid (0.15 mg/mL; 10 kDa) has been dissolved in 1.7 mL mQ water, and NHS (0.6 µmol, 10 µL of 6.9 mg/mL fresh stock in water) had been added. The mixture was stirred overnight at 1000 rpm, and afterwards 1× bicarbonate (pH 8.0; 200 µL), methoxy-PEG-amine (0.3 µmol; Polysciences, 26026-1) were added, in a total volume of 2.3 mL. The reaction was stirred at room temperature, 1000 rpm, in dark, overnight, and worked up using Amicon 10 kDa MWKO, following the manufacturer's protocol. The product has been reconstituted in 2 mL 1×PBS, pH 5.

Step 3. Complexation of chitosan with hyaluronic acid: Product of step 1 (1 mL) has been mixed with step 2 product (1 mL) in the buffers mentioned above. The mixture was kept under 1000 rpm shaking, room temperature, for 30 min, and purified by 50 kDa MWKO Amicon, following the manufacturer's protocol.

Nanosight experiment: Nanosight measurement was done in Jang lab, DTU, using Nano sight equipment NTA Version: NTA 3.1 Build 3.1.46 with Script SOP Standard Measurement 03-47-19PM 20D. The cell of the equipment must be cleaned and unscrewed totally by ethanol and Millipore water. 500 µL diluted sample was injected three times for three run and the concentration of Nanoparticles was adjusted using water pH 6 if the concentration of samples doesn't fit the analysis. The size distribution data and the size with maximum number of particles were recorded, see FIG. 10.

Scanning Electron Microscopy (SEM): The morphology of the Chitosan nanoparticles (NP) was investigated using a Quanta FEG 3D scanning electron microscope (SEM). Samples were attached on metal stubs with double-sided adhesive carbon tape and coated with 6 nm of gold for better conductivity using a sputter coater (Leica Coater ACE 200). The average NP diameter was calculated using image J analysis software (National Institutes of Health, MD, USA) measured at different NP for each image.

Figure 10C:
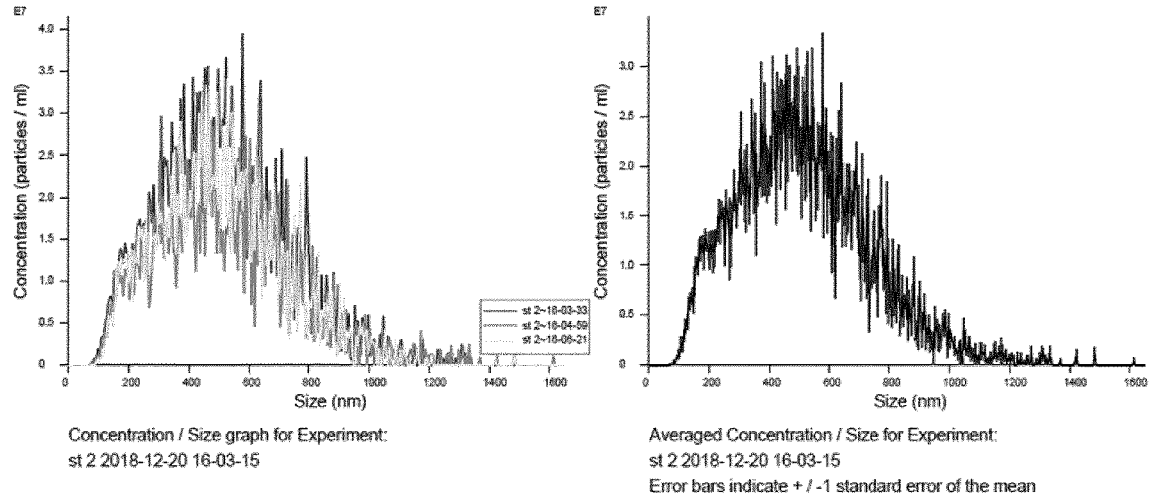
FIG. 10: Nanosight experiment of Chitosan/Hyaluronic acid/PEG/PEP2 nanoconjugates: size distribution data and the size with maximum number of particles. A) CH/HA control, B) covalent attachment of peptide, C) non-covalent attachment of peptide.
Figure 11A:
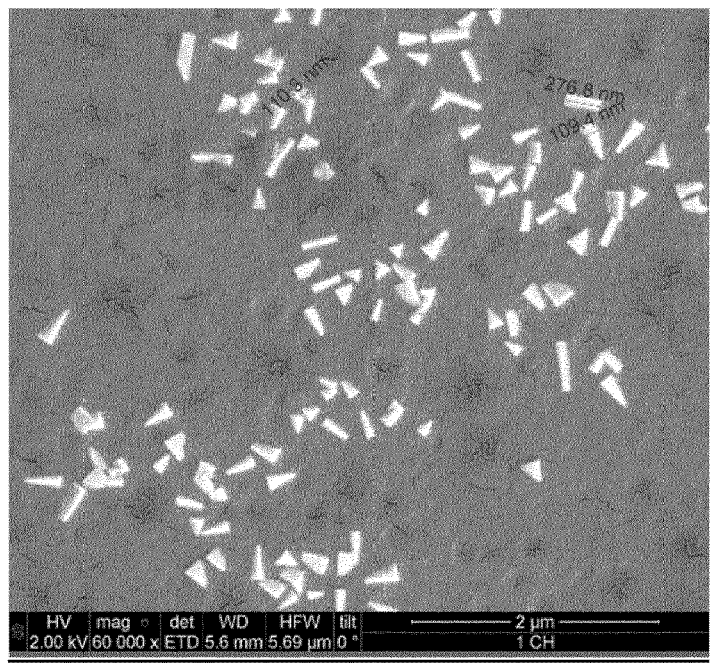
FIG. 11: Scanning Electron Microscopy data of Chitosan/Hyaluronic acid/PEG/PEP2 nanoconjugates A) covalent attachment of peptide: average nanoparticle size is 100-300 nm. B) non-covalent attachment of peptide: average nanoparticle size is 520 nm.
Figure 11B:
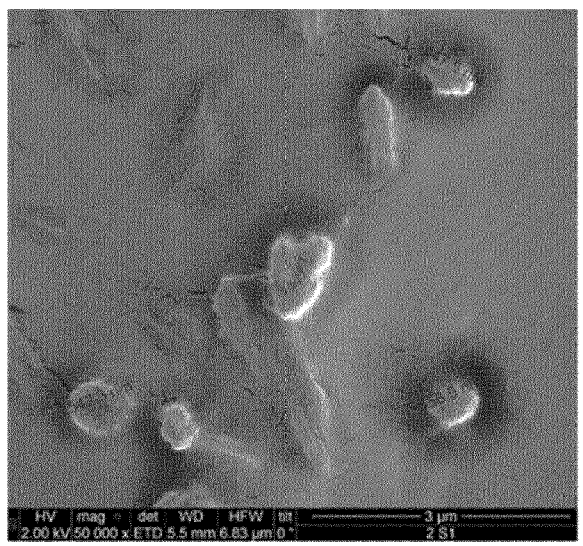
Figure 11B:
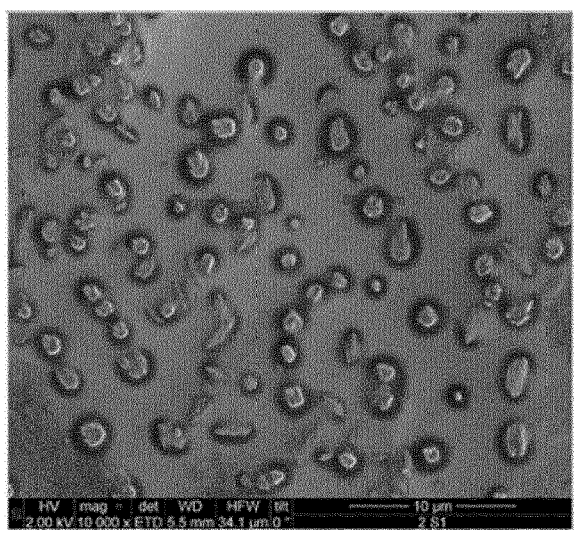

The average nanoparticle size was 100-300 nm for the covalently attached complex (FIG. 11A) which matches with the measurement of nanosight (FIG. 10B), while the average nanoparticle size was 520 nm for the non-covalently attached complex (FIG. 11B) which similarly matches with the measurement of nanosight (FIG. 10C).

ELISA Testing of PEP2-Nanoconjugates:

Prior to ELISA, total amount of protein in each sample was estimated by Bradford method using standard curve of BSA control at known concentration (BioRad). In a maxisorb 96 well plate controls (BSA standard samples at concentrations 2 mg/mL, 1 mg/mL, 0.5 mg/mL and 0.1 mg/mL) and plasma sample were mixed with a Bradford reagent following manufacturer's protocol (BioRad). Plasma samples were used in dilution 1:100. Resulting absorbances at 595 nm were measured on Magellan Tecan microplate reader. Total amount of protein was calculated using standard curve.

ELISA: Maxisorb 96 well plates (NUNC Thermofisher) were coated with nanoparticle antigens/controls at concentration 8 µg/mL in 1×PBS overnight (room temperature; 100 µl/well). After washing with 1×PT (2×300 µl/well, PT: 50 µl Tween-20 in 1 L 1×PBS), the plates were blocked with 1×PTB (1 h, 37° C.; 100 µl/well, PTB: 20 g BSA, 50 µl Tween-20 in 1 L 1×PBS). Incubation with plasma at desired dilution was performed at room temperature for 1.5 h using diluent: 2 g BSA, 50 µl Tween-20 in 1 L 1×PBS (100 µl/well). This was followed by washing (2×300 µl 1×PBS) and incubation with HPR-labelled secondary antibody for 1.5 h at room temperature using same diluent and dilution of the secondary antibody provided by supplier (HPR-conjugated a-aIgG; Sigma). Subsequent washing (2×300 µl PT) and incubation with freshly prepared TMB-$H_2O_2$ solution (Sigma; 100 µl/well) was followed by adding a stop solution (1M H2SO4; 50 µl/well) and reading resulting absorbance values at 450 nm on Magellan Tecan microplate reader. Linear range for each antigen was determined via testing series of control dilutions (SLE and healthy controls in dilutions 1:50 to 1:2000). According to the results plasma dilutions 1:100-1:500 were within linear range of the assay for each antigen ($R2>0.95$).

Results of ELISA screening for antigen PEP2 and NPs prepared as described above is presented in table 11.

TABLE 11

Results of ELISA screening for nanoconjugates comprising antigen PEP2

| Parameter | Healthy | Disease control SLE | Patients with RA |
|---|---|---|---|
| Number of individuals | 30 | 30 | 30 |
| Female, n (%) | 22 (73) | 23 (77) | 30 (100) |
| Age, median (range) | 33.4 (29-56) | 33 (20-44) | 32 (26-51) |
| Anti-CCP2, n (%)[b] - commercial ELISA | 5 (17) | 7 (23) | 12 (40) |
| Anti-cit-Fib protein, n (%) - commercial ELISA | 2 (7) | 4 (13) | 15 (50) |
| a-PEP2, n (%) | 0 (0) | 2 (7) | 17 (57) |
| a-NP1, n (%) | 1 (3) | 2 (7) | 17 (57) |
| a-NP2, n (%) | 2 (7) | 2 (7) | 16 (53) |

The invention claimed is:

1. A nanoconjugate complex comprising: i) at least one autoantigen, wherein the autoantigen comprises SEQ ID NO:10, ii) a nanocarrier, wherein the nanocarrier is chitosan, and iii) at least one helper moiety, wherein the helper moiety is hyaluronic acid.

2. The nanoconjugate complex according to claim 1, wherein at least one link connects the autoantigen to the helper moiety or to the nanocarrier—by covalent or non-covalent binding, and wherein the at least one link comprises at least one functional group selected from the group consisting of an ether, an ester, a disulfide, an amide, a 1,2,3-triazole, a PEG, a phospholipid and an electrostatic interaction.

3. The nanoconjugate complex according to claim 1, wherein the nanoconjugate complex has a size of 100 to 500 nm.

4. A pharmaceutical composition comprising a nanoconjugate complex according to claim 1.

5. The nanoconjugate complex according to claim 1, for use in treating: rheumatoid arthritis (RA).

6. A method of treating a subject suffering from rheumatoid arthritis, comprising: administering the pharmaceutical composition according to claim 4 to said subject.

* * * * *